US011096396B2

(12) United States Patent
Nielsen et al.

(10) Patent No.: US 11,096,396 B2
(45) Date of Patent: Aug. 24, 2021

(54) LACTOBACILLUS FERMENTUM BACTERIA WITH ANTIFUNGAL ACTIVITY

(71) Applicant: Chr. Hansen A/S, Hoersholm (DK)

(72) Inventors: Cecilie Lykke Marvig Nielsen, Broenshoej (DK); Tina Hornbaek, Birkeroed (DK); Pia Rasmussen, Roedovre (DK); Lone Poulsen, Toelloese (DK); Thomas Eckhardt, Birkeroed (DK); Gunnar Oeregaard, Vaerloese (DK); Elahe Ghanei Moghadam, Glostrup (DK)

(73) Assignee: CHR. HANSEN A/S, Hoersholm (DK)

( * ) Notice: Subject to any disclaimer, the term of this patent is extended or adjusted under 35 U.S.C. 154(b) by 104 days.

(21) Appl. No.: 16/128,460

(22) Filed: Sep. 11, 2018

(65) Prior Publication Data

US 2019/0059406 A1 Feb. 28, 2019

Related U.S. Application Data

(63) Continuation of application No. 15/755,023, filed as application No. PCT/EP2016/070381 on Aug. 30, 2016.

(30) Foreign Application Priority Data

Aug. 31, 2015 (EP) .................................... 15183198

(51) Int. Cl.
*A23C 9/123* (2006.01)
*A61K 35/747* (2015.01)
(Continued)

(52) U.S. Cl.
CPC ............ *A23C 9/1234* (2013.01); *A23K 10/18* (2016.05); *A23L 33/135* (2016.08);
(Continued)

(58) Field of Classification Search
None
See application file for complete search history.

(56) References Cited

U.S. PATENT DOCUMENTS

2010/0009034 A1* 1/2010 Ling .................... A23C 9/1234
426/43
2010/0028492 A1* 2/2010 Mogna ..................... A23C 3/03
426/43

(Continued)

FOREIGN PATENT DOCUMENTS

WO WO-2011/000879 A2 1/2011
WO WO-2012/007978 A2 1/2012
(Continued)

OTHER PUBLICATIONS

Gerbaldo et al., "Antifungal activity of two Lactobacillus strains with potential probiotic properties," FEMS Microbiol Lett 332 (2012) 27-33.
(Continued)

*Primary Examiner* — Felicia C Turner
(74) *Attorney, Agent, or Firm* — Foley & Lardner LLP

(57) ABSTRACT

Disclosed is Bacterium of the species *Lactobacillus rhamnosus* CHCC15860 as deposited with the German Collection of Microorganisms and Cell Cultures (DSMZ) under accession No. DSM32092. Also disclosed are compositions comprising the bacterium, methods for producing fermented milk products using the bacterium and the products thus obtained.

14 Claims, 21 Drawing Sheets

(51) Int. Cl.
*C12N 1/20* (2006.01)
*A23K 10/18* (2016.01)
*A23L 33/135* (2016.01)
*C12R 1/225* (2006.01)

(52) U.S. Cl.
CPC .............. *A61K 35/747* (2013.01); *C12N 1/20* (2013.01); *C12N 1/205* (2021.05); *A23V 2002/00* (2013.01); *A23Y 2220/35* (2013.01); *C12R 2001/225* (2021.05)

(56) References Cited

U.S. PATENT DOCUMENTS

| | | | |
|---|---|---|---|
| 2014/0004083 A1* | 1/2014 | Hollard | A01N 1/0221 424/93.4 |
| 2014/0023749 A1* | 1/2014 | Jimenez | A23L 27/88 426/43 |
| 2018/0235248 A1 | 8/2018 | Nielsen et al. | |
| 2018/0235249 A1 | 8/2018 | Nielsen et al. | |
| 2018/0249727 A1 | 9/2018 | Nielsen et al. | |

FOREIGN PATENT DOCUMENTS

| | | | |
|---|---|---|---|
| WO | WO-2012/136830 A1 | 10/2012 | |
| WO | WO-2013/153070 A1 | 10/2013 | |

OTHER PUBLICATIONS

Aunsbjerg et al., "Contribution of Volatiles to the Antifungal Effect of Lactobacillus Paracasei in Defined Medium and Yogurt", International Journal of Food Microbiology (2015) vol. 194, pp. 46-53 (Available online Nov. 2014).

Gerez et al., "Control of Spoilage Fungi by Lactic Acid Bacteria", Biological Control, (Nov. 2012) vol. 64, No. 3, pp. 231-237.

Voulgari et al., "Antifungal Activity of Non-Starter Lactic Acid Bacteria Isolates From Dairy Products", Food Control (Feb. 2010) vol. 21, No. 2, pp. 136-142.

* cited by examiner

LACTOBACILLUS FERMENTUM BACTERIA WITH ANTIFUNGAL ACTIVITY

CROSS-REFERENCE TO RELATED APPLICATIONS

The present application is a continuation of U.S. application Ser. No. 15/755,023, filed Feb. 23, 2018, which is the U.S. National Stage of International Application PCT/EP2016/070381, filed Aug. 30, 2016, and claims priority to European Patent pplication No. 15183198.9, filed Aug. 31, 2015.

FIELD OF THE INVENTION

The present invention relates to *Lactobacillus fermentum* bacteria with antifungal activity, compositions comprising the bacteria, in particular adjunct cultures comprising the bacteria, methods of producing a fermented milk product using the bacteria or the cultures and the fermented milk products thus obtained, including food, feed and pharmaceutical products.

BACKGROUND OF THE INVENTION

Lactic acid bacteria (LAB) have been used in decades for increasing the shelf life of food products. During fermentation LAB produce lactic acid as well as other organic adds which cause a reduction of pH of the fermented product. Products having an acidic pH do not support further growth of most microorganisms, including pathogenic and spoilage bacteria. However, growth of yeasts and moulds is not affected by low pH and often cause spoilage of fermented dairy products.

In addition to the production of organic adds some LAB also produce metabolites with antimicrobial and in particular antifungal activity.

For example, European Patent Application no. EP0221499 describes the antifungal properties of *Lactobacillus rhamnosus* NRRL-B-15972 which is capable of inhibiting the growth of different molds when cultured on agar medium supplemented with cucumber juice. Similarly, European Patent Application no. EP0576780 relates to *Lactobacillus rhamnosus* LC-705 a strain that apparently inhibits the growth of *Penicillium, Cladosporium, Fusarium* and *Candida* on a lactoserum-based medium, supplemented with casein hydrolysate and with yeast extract. European Patent Application no. EP1442113 describes mixtures of *Propionibacterium jensenii* and *Lactobacillus* sp., such as *Lactobacillus rhamnosus*, with antimicrobial effects and their use for bioprotection. European Patent Application no. EP13717237 describes *Lactobacillus paracasei* strains with antifungal effects and European Patent Application no. EP13714671 describes *Lactobacillus rhamnosus* strains with antifungal effects.

An overview of LAB with antifungal effects and their use for the protection of bread and fruits is provided by Gerez et al., 2013.

Cultures with antifungal effects are further commercially available and include FreshQ® cultures of Chr. Hansen as well as cultures of Dupont, SACCO and Bioprox. Developing cultures with antifungal effects represents a big challenge, as it requires the identification of cultures that provide significant antifungal effect in real food applications. Another factor that needs careful evaluation in the selection of bioprotective culture candidates, is the effect on sensory properties of the food product. A problem that has been identified in the commercial products is the extent of post acidification, i.e. continuation of acidification by the culture after the product has reached the desired pH. This represents a problem in particular at elevated storage temperatures, during holding of the fermented product in fermentation tanks before product cooling or during maturation steps.

Commercial bioprotective cultures were further considered to produce excessive diacetyl flavor component causing a 'creamy' flavor which can be perceived as an undesired flavor impact (Aunsbjerg et al., 2015).

Consequently, there is still a need for new and advantageous food grade bacteria with antifungal effects and minimal flavor impact.

SUMMARY OF THE INVENTION

The present invention provides bacteria of the species *Lactobacillus fermentum* having the ability to inhibit the growth of the fungus *Penicillium solitum* deposited under the accession No.: DSM32093 or the growth of the fungus *Penicillium brevicompactum* deposited under the accession No.: DSM32094 by at least 50%.

By a dedicated effort a new group of *Lactobacillus fermentum* strains was identified that provide significant antifungal effects and additional advantages when used as a bioprotective strain in methods for producing fermented products. A total of 10 different *Lactobacillus fermentum* strains were identified that inhibit the growth of *P. solitum* or *P. brevicompactum* by at least 50%.

The *Lactobacillus fermentum* strains of the present invention may further be characterized in having the ability to reduce the concentration of acetaldehyde produced by a starter culture during fermentation in a fermented milk product by at least 50%.

In a related embodiment the *Lactobacillus fermentum* strains of the present invention can further be characterized in that the bacterium secretes only low amounts of diacetyl, for example in a range of 0 to 5 ppm.

*Lactobacillus fermentum* strains of the present invention may alternatively or additionally be characterized in that it increases the pH of a fermented milk product comprising the *Lactobacillus fermentum* during storage after fermentation in comparison to a milk product fermented with the same starter culture not containing the *Lactobacillus fermentum*.

The present invention therefore provides the bacteria as described above, compositions comprising the same, methods using the bacteria for producing fermented milk products, as well as the products thus obtained.

DETAILED DESCRIPTION OF THE INVENTION

The present invention provides a bacterium of the species *Lactobacillus fermentum* having the ability to inhibit the growth of the fungus *Penicillium solitum* deposited under the accession No.: DSM32093 or the growth of the fungus *Penicillium brevicompactum* deposited under the accession No.: DSM32094 by at least 50%. In a preferred the present invention relates to a bacterium of the species *Lactobacillus fermentum* having the ability to inhibit the growth of the fungus *Penicillium solitum* deposited under the accession No.: DSM32093 or the growth of the fungus *Penicillium brevicompactum* deposited under the accession No.: DSM32094 by at least 50% when grown in milk or a milk based substrate, such as e.g. a fermented dairy product. The ability to inhibit the growth of a fungus can be determined by numerous different assays known in the art. In the context of the present invention the ability to inhibit the growth of the fungus *Penicillium solitum* deposited under the accession No.: DSM32093 or the growth of the fungus *Penicillium brevicompactum* deposited under the accession No.: DSM32094 by at least 50% is preferably determined using an assay comprising:

(1) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and
  (c) solidifying the fermented milk by the addition of agar;
(2) generating at least one spot of the *P. solitum* or the *P. brevicompactum* on the agar solidified fermented milk with a concentration of 500 spores/spot and incubating the same for 7 days at 25° C.;
(3) determining the percent inhibition by determining the largest diameter of the colony formed by growth of the *P. solitum* or *P. brevicompactum* and expressing the diameter as percent of the largest diameter formed under the same conditions but in the absence of the *Lactobacillus fermentum* strain.

The *Lactobacillus fermentum* strains of the present invention have particular advantages as they increase the storage stability of food products made with these bacteria. In one alternative the *Lactobacillus fermentum* strains of the present invention inhibit the growth of the fungus *Penicillium solitum* deposited under the accession No.: DSM32093 and the growth of the fungus *Penicillium brevicompactum* deposited under the accession No.: DSM32094 by at least 50%. In a related embodiment the *Lactobacillus fermentum* strains of the present invention inhibit the growth of the fungus *Penicillium solitum* deposited under the accession No.: DSM32093 and/or the growth of the fungus *Penicillium brevicompactum* deposited under the accession No.: DSM32094 by at 60%, at least 70% or at least 75%.

It should be understood that the concentration of at least $10^7$ CFU/g of the *Lactobacillus fermentum* strains of the present invention identified in the above assay represents a concentration providing excellent antifungal effects. While the invention therefore encompasses the *Lactobacillus fermentum* strains of the present invention in a concentration of at least $10^7$ CFU/g, such as in a concentration of $10^7$ CFU/g to $10^{11}$ CFU/g, $10^7$ CFU/g to CFU/g and $10^7$ CFU/g to $10^9$ CFU/g, the invention is not limited to these concentrations, as good antifungal effects were also obtained with a lower concentration.

According to one aspect the bacteria of the invention are further characterized in secreting low amounts or essentially no volatile compounds, which affect the sensory properties of the food product. Common starter cultures, such as commercially available mixtures of *Streptococcus thermophilus* and *Lactobacillus delbrueckii* subsp. *bulgaricus* are known to produce volatile compounds which contribute significantly to the sensory properties of the fermented products. Acetaldehyde, diacetyl and acetoin for example are known volatile compounds, which affect the sensory properties of the food product. In a related embodiment the bacteria of the present invention are characterized in reducing the presence of acetaldehyde as produced by other bacteria in the starter culture. For example, certain *Lactobacillus fermentum* strains of the present invention may further be characterized in having the ability to reduce the concentration of acetaldehyde produced by a starter culture during fermentation in a fermented milk product by at least 50%. The reduction is thus determined in comparison to a fermented product produced without the *Lactobacillus fermentum* strains of the present invention. Different assays are known in the art for determining the concentration of acetaldehyde in a fermented product and can be used for that purpose in accordance with the present invention. The ability to reduce the concentration of acetaldehyde produced by a starter culture during fermentation in a fermented milk product by at least 50% is preferably determined in an assay comprising:

(1) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and;
(2) storing the fermented milk product at 7±1° C. for 14 days;
(3) adding 200 µl of 4N $H_2SO_4$ to 1 g of the fermented milk product and determining the concentration of acetaldehyde by static head space gas chromatography.

Acetaldehyde is a taste component produced by lactic add bacteria during fermentation. While the component is desirable in certain applications, it would be advantageous to reduce or avoid the presence of acetaldehyde in other applications. *Lactobacillus fermentum* bacteria reducing the concentration of acetaldehyde in a fermented milk product therefore provide advantages in specific applications, for example when preparing mild or sweetened yoghurt. The *Lactobacillus fermentum* strains of the present invention may for example reduce the concentration of acetaldehyde produced by a starter culture during fermentation in a fermented milk product by at least 75%, at least 95% or at least 98%.

Alternatively or additionally, the *Lactobacillus fermentum* strains of the present invention can be characterized in that the bacterium secretes diacetyl in a range of 0 to 5 ppm. The secretion of diacetyl can be determined using different assays known in the art, but is preferably determined in an assay comprising:

(1) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and;
(2) storing the fermented milk product at 7±1° C. for 14 days;
(3) adding 200 µl of 4N $H_2SO_4$ to 1 g of the fermented milk product and determining the concentration of diacetyl by static head space gas chromatography.

*Lactobacillus fermentum* bacteria secreting low concentrations of diacetyl have advantages in methods of producing food products with these bacteria, as other strains exerting antifungal activity that produce high concentrations of these volatile compounds affect the taste of the final product and can therefore not be used for all applications. *Lactobacillus fermentum* strains of the present invention can be characterized in that the bacterium secretes diacetyl in a range of 0 to 3 ppm or 0 to 2 ppm.

The *Lactobacillus fermentum* strains of the present invention may be characterized by additional advantageous effects. For example, the strains can be characterized in that it increases the pH (i.e. counteracts the postacidification) of a fermented milk product comprising the *Lactobacillus fermentum* during storage after fermentation in comparison to a milk product fermented with the same starter culture not containing the *Lactobacillus fermentum*. The increase in pH is at least by a value of 0.1 and is preferably determined after storing the fermented product over 21 days at 25° C. As indicated above, prior art antifungal bacteria were observed to contribute to post-acidification. The inventors surprisingly found that the *Lactobacillus fermentum* strains of the present invention do not only fail to contribute to post-acidification, but actually antagonize post-acidification by increasing the pH value. As is shown in the Examples, below, the effect is particularly notable in fermentation processes using starter cultures exhibiting significant post-acidification, including a number of commercially available starter cultures and in particular when used together with commercial antifungal bacteria.

The *Lactobacillus fermentum* strains of the present invention can for example be characterized in that they increase the pH of a fermented milk product comprising the *Lactobacillus fermentum* during storage after fermentation in comparison to a milk product fermented with the same starter culture not containing the *Lactobacillus fermentum*, wherein the increase in pH is at least by a value of 0.1 and is determined after storing the fermented product over 21 days at 25° C., and wherein the starter culture comprises LAB which are able to decrease the pH of a milk product during fermentation to a value of pH 4.6 in 10 hours or less. For example, the assay may be based on mixtures of *Streptococcus thermophilus* and *Lactobacillus delbrueckii* subsp. *bulgaricus*. Respective mixtures are frequently used for the production of yoghurt and known to cause post-acidification.

In a related embodiment a fermented milk product comprising the *Lactobacillus fermentum* maintains a pH above 4.0 when stored for at least 14 days at 25° C., wherein the fermented milk product is obtained by a method comprising inoculating a milk with the *Lactobacillus fermentum* in a concentration of at least $10^7$ CFU/g and with a starter culture, fermenting until a pH of 4.6 is reached, shaking the fermented product and cooling. These *Lactobacillus fermentum* strains of the present invention therefore reduce the post-acidification effect observed in prior art bioprotective cultures and even in conventional starter cultures. It should be understood that the feature specifying that the *Lactobacillus fermentum* strains of the present invention may maintain the pH above 4.0 when stored for at least 14 days at 25° C. merely characterizes the assay generally used to determine the effect. It is not necessary or required that the *Lactobacillus fermentum* strains of the present invention, compositions comprising the same, including food or feed products are in fact stored under these conditions. Again, in one aspect the assay can be carried out using a starter culture comprising LAB which are able to decrease the pH of a milk product during fermentation to a value of pH 4.6 in 10 hours or less. For example, the assay may be based on mixtures of *Streptococcus thermophilus* and *Lactobacillus delbrueckii* subsp. *bulgaricus*.

Bacteria of the present invention may advantageously be derived from one of the following deposited strains:

(a) the *Lactobacillus fermentum* strain CHCC12798 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32084;

(b) the *Lactobacillus fermentum* strain CHCC12797 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32085;

(c) the *Lactobacillus fermentum* strain CHCC14591 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32086;

(d) the *Lactobacillus fermentum* strain CHCC14588 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32087;

(e) the *Lactobactillus fermentum* strain CHCC15844 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32088;

(f) the *Lactobacillus fermentum* strain CHCC15865 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32089;

(g) the *Lactobacillus fermentum* strain CHCC15847 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32090;

(h) the *Lactobactillus fermentum* strain CHCC15848 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32091;

(i) the *Lactobacillus fermentum* strain CHCC15926 as deposited at German Collection of Microorganisms and Cell Cultures (Deutsche Sammlung von Mikroorganismen und Zellkulturen GmbH; DSMZ), Inhoffenstr. 7B, D-38124 Braunschweig under the accession No.: 32096;

(j) the *Lactobacillus fermentum* strain CHCC2008 as deposited at German Collection of Microorganisms and Cell Cultures (Deutsche Sammlung von Mikroorganismen und Zellkulturen GmbH; DSMZ), Inhoffenstr. 78, D-38124 Braunschweig under the accession No.: 22584;

(k) a mutant strain obtainable from one the deposited bacteria according to (a) to (j), wherein the mutant has the ability to inhibit the growth of the fungus *Penicillium solitum* deposited at DSMZ under the accession No.: 32093 or the growth of the fungus *Penicillium brevicompactum* deposited at DSMZ under the accession No.: 32094 by at least 50% in an assay comprising:

(1) preparing a fermented milk product by:
  (a) inoculating milk with the *Lactobacillus fermentum* in a concentration of at least $10^7$ CFU/g and with a starter culture,
  (b) fermenting until a pH of 4.6 is reached, and
  (c) solidifying the fermented milk by the addition of agar;

(2) generating at least one spot of the *P. solitum* or the *P. brevicompactum* on the agar solidified fermented milk with a concentration of 500 spores/spot and incubating the same for 7 days at 25° C.;

(3) determining the percent inhibition by determining the largest diameter of the colony formed by growth of the *P. solitum* or *P. brevicompactum* and expressing the diameter as percent of the largest diameter formed under the same conditions but in the absence of the *Lactobacillus fermentum* strain.

In the context of the present application, the term "lactic acid bacteria" or "LAB" is used to refer to food-grade bacteria producing lactic acid as the major metabolic end-product of carbohydrate fermentation. These bacteria are related by their common metabolic and physiological characteristics and are usually Gram positive, low-GC, acid tolerant, non-sporulating, non-respiring, rod-shaped bacilli or cocci. During the fermentation stage, the consumption of lactose by these bacteria causes the formation of lactic acid, reducing the pH and leading to the formation of a protein coagulum. These bacteria are thus responsible for the acidification of milk and for the texture of the dairy product. As used herein, the term "lactic acid bacteria" encompasses, but is not limited to, bacteria belonging to the genus of *Lactobacillus* spp., *Bifidobacterium* spp., *Streptococcus* spp., *Lactococcus* spp., such as *Lactobacillus delbrueckii* subsp. *bulgaricus, Streptococcus thermophilus, Lactobacillus lactis, Bifidobacterium animalis, Lactococcus lactis, Lactobacillus paracasei, Lactobacillus plantarum, Lactobacillus helveticus, Lactobacillus acidophilus, Bifidobacterium breve* and *Leuconostoc* spp.

Depending on the optimum temperature for propagation, LAB are characterized as mesophilic or thermophilic LAB. The term "mesophile" refers to microorganisms that thrive best at moderate temperatures. The term "mesophilic fermentation" herein refers to fermentation at a temperature between about 22° C. and about 35° C. The term "mesophilic fermented milk product" refers to fermented milk products prepared by mesophilic fermentation of a mesophilic starter culture and include such fermented milk products as buttermilk, sour milk, cultured milk, smetana, sour cream and fresh cheese, such as quark, tvarog and cream cheese. The industrially most useful mesophilic bacteria include *Lactococcus* spp. and *Leuconostoc* spp.

The term "thermophile" refers to microorganisms that thrive best at high temperatures. The term "thermophilic fermentation" refers to fermentation methods carried out at a temperature between about 35° C. and about 45° C. The term "thermophilic fermented milk product" refers to fermented milk products prepared by thermophilic fermentation using a thermophilic starter culture and include such fermented milk products as set-yoghurt, stirred-yoghurt, strained yoghurt and drinking yoghurt. The industrially most useful thermophilic bacteria include *Streptococcus* spp. and *Lactobacillus* spp.

As will be outlined below, the present invention encompasses methods using mesophilic and thermophilic fermentation.

The terms "inhibit" in relation to fungi, yeasts and molds refers to a decrease in the growth or sporulation or a reduction in the number or in the concentration of fungi, yeasts and molds, for example in food products and/or on the surface of food products comprising the bacteria of the present invention in relation to food products which do not comprise such bacteria. The extent of inhibition provided by the *Lactobacillus fermentum* bacteria of the present invention is preferably determined by growth on agar solidified fermented milk in the presence and absence of the *Lactobacillus fermentum* bacteria.

In the present context, the term "mutant" should be understood as a strain derived from a strain of the invention by means of e.g. genetic engineering, radiation and/or chemical treatment. It is preferred that the mutant is a functionally equivalent mutant, e.g. a mutant that has substantially the same, or improved, properties in particular in relation to the antifungal properties, as the deposited strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 5%, or less than 1% or even less than 0.1% of the nucleotides in the bacterial genome have been shifted with another nucleotide, or deleted, compared to the mother strain.

The use of the terms "a" and "an" and "the" and similar referents in the context of describing the invention (especially in the context of the following claims) are to be construed to cover both the singular and the plural, unless otherwise indicated herein or clearly contradicted by context.

The present invention further provides compositions comprising at least one bacterium of the species *Lactobacillus fermentum* with the ability to inhibit the growth of the fungus *Penicillium solitum* CHCC16948 deposited at DSMZ under the accession No.: 32093 or the growth of the fungus *Penicillium brevicompactum* CHCC16935 deposited at DSMZ under the accession No.: 32094 on an agar solidified fermented milk by at least 50% in the assay as described above.

Respective compositions may comprise numerous further bacteria including LABS. A preferred composition of the present invention is therefore characterized in that the composition further comprises at least one further bacterium selected from one or more of the following genera and species *Lactobacillus* spp., *Bifidobacterium* spp., *Streptococcus* spp., *Lactococcus* spp., such as *Lactobacillus delbrueckii* subsp. *bulgaricus, Streptococcus thermophilus, Lactobacillus Bifidobacterium animalis, Lactococcus lactis, Lactobacillus paracasei, Lactobacillus plantarum, Lactobacillus helveticus, Lactobacillus acidophilus, Bifidobacterium breve* and *Leuconostoc* spp.

In a particularly preferred embodiment, the compositions of the present invention comprise at least one bacterium of the species *Lactobacillus fermentum* with antifungal activity as described above and one or more second bacterium with antifungal activity. In one embodiment, several different strains of the *Lactobacillus fermentum* bacteria with antifungal activity of the present invention are combined. Alternatively, these further bacteria can for example be selected from:

(a) *Lactobacillus rhamnosus* bacterium of strain CHCC15860 as deposited with the German Collection of Microorganisms and Cell Cultures (DSMZ) under accession No. DSM32092;

(b) *Lactobacillus rhamnosus* bacterium of strain CHCC5366 as deposited with the German Collection of Microorganisms and Cell Cultures (DSMZ) under accession No. DSM23035;

(c) *Lactobacillus rhamnosus* bacterium of strain CHCC12697 as deposited with the German Collection of Microorganisms and Cell Cultures (DSMZ) under accession No. DSM24616;

(d) *Lactobacillus paracasei* bacterium of strain CHCC12777 as deposited with the German Collection of Microorganisms and Cell Cultures (DSMZ) under accession No. DSM24651; and (e) *Lactobacillus paracasei* bacterium of strain CHCC14676 as deposited with the German Collection of Microorganisms and Cell Cultures (DSMZ) under accession No. DSM25612.

The present inventors found additive antifungal effects for these strains and a surprising synergistic antifungal effect caused by a combination of *Lb. rhamnosus* CHCC15860 and *Lb. fermentum* CHCC14591 in comparison to the inhibitory effect of each strain used alone.

The compositions of the present invention may in addition comprise numerous further components, including one or more cryoprotective compounds as well as flavoring compounds.

LAB are most commonly added in the form of a starter culture to milk. The term "starter" or "starter culture" as used in the present context refers to a culture of one or more food-grade micro-organisms, in particular lactic acid bacteria, which are responsible for the acidification of the milk base. Starter cultures may be fresh, but are most frequently frozen or freeze-dried. These products are also known as "Direct Vat Set" (DVS) cultures and are produced for direct inoculation of a fermentation vessel or vat for the production of a dairy product, such as a fermented milk product or a cheese. Respective starter cultures are commercially available from numerous sources and include F-DVS YoFlex Mild 2.0, F-DVS YF-L901, FD-DVS YF-812 and F-DVS CH-1, four cultures commercially available from Chr. Hansen containing mixtures of *Streptococcus thermophilus* and *Lactobacillus delbrueckii* subsp. *bulgaricus*.

In one aspect the present invention therefore provides compositions in the form of a solid frozen or freeze-dried starter culture comprising lactic acid bacteria in a concentration of at least $10^9$ colony forming units per g of frozen material or in a concentration of at least $10^{10}$ colony forming units per g of frozen material or in a concentration of at least $10^{11}$ colony forming units per g of frozen material which compositions include a bacterium of the species *Lactobacillus fermentum* with antifungal activity as described above.

The present invention further provides *Lactobacillus fermentum* bacteria and compositions comprising the same which are characterized by more than one of the above features and compositions comprising the same. For example, the present invention provides a bacterium of the species *Lactobacillus fermentum* having the ability to inhibit the growth of the fungus *Penicillium solitum* deposited under the accession No.: DSM32093 or the growth of the fungus *Penicillium brevicompactum* deposited under the accession No.: DSM32094 by at least 50% determined in an assay comprising:

(1) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and
  (c) solidifying the fermented milk by the addition of agar;
(2) generating at least one spot of the *P. solitum* or the *P. brevicompactum* on the agar solidified fermented milk with a concentration of 500 spores/spot and incubating the same for 7 days at 25° C.;
(3) determining the percent inhibition by determining the largest diameter of the colony formed by growth of the *P. solitum* or *P. brevicompactum* and expressing the diameter as percent of the largest diameter formed under the same conditions but in the absence of the *Lactobacillus fermentum* strain;

and further characterized in that the bacterium of the species *Lactobacillus fermentum* secretes diacetyl in a range of 0 to 5 ppm, wherein the concentration of diacetyl is determined in an assay comprising:

(4) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and;
(5) storing the fermented milk product at 7±1° C. for 14 days;
(6) adding 200 µl of 4N $H_2SO_4$ to 1 g of the fermented milk product and determining the concentration of diacetyl by static head space gas chromatography.

These bacteria may further be characterized in the ability to reduce the concentration of acetaldehyde produced by a starter culture during fermentation in a fermented milk product by at least 50%.

Alternatively, or additionally, the bacteria of the species *Lactobacillus fermentum* can further be characterized in that it increases the pH of a fermented milk product comprising the *Lactobacillus fermentum* during storage after fermentation in comparison to a milk product fermented with the same starter culture not containing the *Lactobacillus fermentum*.

In a separate embodiment the invention further provides a *Lactobacillus fermentum* bacterium having the ability to inhibit the growth of the fungus *Penicillium solitum* deposited under the accession No.: DSM32093 or the growth of the fungus *Penicillium brevicompactum* deposited under the accession No.: DSM32094 by at least 50% determined in an assay comprising:

(1) preparing a fermented milk product by:
  (a) inoculating a milk with the *Lactobacillus fermentum* in a concentration of at least $10^7$ CFU/g and with a starter culture,
  (b) fermenting until a pH of 4.6 is reached, and
  (c) solidifying the fermented milk by the addition of agar,
(2) generating at least one spot of the *P. solitum* or the *P. brevicompactum* on the agar solidified fermented milk with a concentration of 500 spores/spot and incubating the same for 7 days at 25° C.;
(3) determining the percent inhibition by determining the largest diameter of the colony formed by growth of the *P. solitum* or *P. brevicompactum* and expressing the diameter as percent of the largest diameter formed under the same conditions but in the absence of the *Lactobacillus fermentum* strain, and further characterized in that the bacterium of the species *Lactobacillus fermentum* increases the pH of a fermented milk product comprising the *Lactobacillus fermentum* during storage after fermentation in comparison to a milk product fermented with the same starter culture not containing the *Lactobacillus fermentum*, wherein the increase in pH is at least by a value of 0.1, and wherein the increase in pH is determined after storing the fermented product over 21 days at 25° C. Again, in one embodiment these bacteria may further have the ability to reduce the concentration of acetaldehyde produced by a starter culture during fermentation in a fermented milk product by at least 50%.

In a further embodiment the present invention provides methods of producing a fermented milk product which comprise adding the *Lactobacillus fermentum* bacterium with antifungal activity as described above or the composition comprising the same to milk or to a milk product and fermenting the mixture at a temperature between about 22° C. and about 43° C. until a pH of less than 4.6 is reached.

In the context of the present application, the term "milk" is broadly used in its common meaning to refer to liquids produced by the mammary glands of animals or by plants. In accordance with the present invention the milk may have been processed and the term "milk" includes whole milk, skim milk, fat-free milk, low fat milk, full fat milk, lactose-reduced milk, or concentrated milk. Fat-free milk is non-fat or skim milk product. Low-fat milk is typically defined as milk that contains from about 1% to about 2% fat. Full fat milk often contains 2% fat or more. The term "milk" is intended to encompass milks from different mammals and plant sources. Mammal sources of milk include, but are not limited to cow, sheep, goat, buffalo, camel, llama, mare and deer. Plant sources of milk include, but are not limited to, milk extracted from soy bean, pea, peanut, barley, rice, oat, quinoa, almond, cashew, coconut, hazelnut, hemp, sesame seed and sunflower seed. In the methods and products of the present invention, milk derived from cows is most preferably used as a starting material for the fermentation.

The term "milk" also includes fat-reduced and/or lactose-reduced milk products. Respective products can be prepared using methods well known in the art and are commercially available (for example from Select Milk Producers Inc., Texas, USA). Lactose-reduced milk can be produced according to any method known in the art, including hydrolyzing the lactose by lactase enzyme to glucose and galactose, or by nanofiltration, electrodialysis, ion exchange chromatography and centrifugation.

The term "milk product" or "milk base" is broadly used in the present application to refer to a composition based on milk or milk components which can be used as a medium for growth and fermentation of LAB. The milk product or base comprises components derived from milk and any other component that can be used for the purpose of growing or fermenting LAB.

The fermentation step of the process for manufacturing fermented dairy products comprises the addition of LAB to milk. Fermentation processes used in production of dairy products are well known and a person of ordinary skill can select fermentation process conditions, including temperature, oxygen, amount and characteristics of microorganism(s) and fermentation time.

Prior to fermentation, the milk substrate may be homogenized and pasteurized according to methods known in the art. "Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices. "Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

In a particularly advantageous method of the present invention the *Lactobacillus fermentum* bacterium with antifungal effects as described above or the composition comprising the same is added to milk or to a milk product and the mixture is fermented in such a manner that (a) the concentration of the *Lactobacillus fermentum* bacteria with antifungal effects is at least $1 \times 10^6$ cfu/g or at least $1 \times 10^7$ cfu/g at the termination of fermentation in the fermented milk product; and/or (b) such that the concentration of the *Lactobacillus fermentum* bacteria with antifungal effects is at least $1 \times 10^5$ cfu/cm$^2$ on the surface of the fermented milk product.

This way of proceeding has the advantage that the antifungal effect of the *Lactobacillus fermentum* bacterium can be fully used.

One way of achieving the concentration is using a method of producing a fermented milk product, wherein the parameters for fermentation are maintained such that the concentration of the *Lactobacillus fermentum* bacteria described above increases during fermentation. Using conventional starter cultures and conditions for fermentation (as described in the Examples) will generally increase the concentration of the *Lactobacillus fermentum* bacteria described above during fermentation by at least 0.5 log. Alternatively, the parameters for fermentation are maintained such that the concentration of the *Lactobacillus fermentum* bacteria described above does not significantly decrease, for example does not decrease by more than 30%, not more than 25%, or not more than 20% during fermentation and storage The present invention also provides the fermentate obtainable by fermenting a milk product with the *Lactobacillus fermentum* bacteria of the present invention. The term fermentate is used to refer to a fermentation product. A respective fermentate can be a liquid obtained from the fermentation process using the *Lactobacillus fermentum* bacteria of the present invention. The liquid can contain bacteria, but does not need to contain the same. The liquid preferably contains the antifungal metabolites produced by the *Lactobacillus fermentum* bacteria of the present invention. The fermentate can be used to produce food, feed or pharmaceutical products. For example, the fermentate may be sprayed on food or feed products to achieve an antifungal effect.

The invention further provides methods of producing a food, feed or pharmaceutical product comprising a method of producing a fermented milk product as described above and the food, feed or pharmaceutical product obtainable by this method.

Fermentation is carried out to produce food products, feed products or pharmaceuticals. The terms "fermented milk product", "food" or "feed" product refer to products obtainable by the fermentation methods of the present invention and include cheese, yoghurt, fruit yoghurt, yoghurt beverage, strained yoghurt (Greek yoghurt, Labneh), quark, fromage frais and cream cheese. The term food further encompasses other fermented food products, including fermented meat, such as fermented sausages, and fermented fish products.

The term "cheese" is understood to encompass any cheese, including hard, semi-hard and soft cheeses, such as cheeses of the following types: Cottage, Feta, Cheddar, Parmesan, Mozzarella, Ernmentaler, Danbo, Gouda, Edam, Feta-type, blue cheeses, brine cheeses, Camembert and Brie. The person skilled in the art knows how to convert the coagulum into cheese, methods can be found in the literature, see e.g. Kosikowski, F. V., and V. V. Mistry, "Cheese and Fermented Milk Foods", 1997, 3rd Ed. F. V. Kosikowski, L. L. C. Westport, Conn. As used herein, a cheese which has a NaCl concentration below 1.7% (w/w) is referred to as a "low-salt cheese".

In the context of the present application, the term "yoghurt" refers to products comprising *Streptococcus thermophilus* and *Lactobacillus delbrueckii* subsp. *bulgaricus* and optionally other microorganisms such as *Lactobacillus delbrueckii* subsp. *lactis, Bifidobacterium animalis* subsp. *lactis, Lactococcus lactis, Lactobacillus acidophilus* and *Lactobacillus paracasei*, or any microorganism derived therefrom. The lactic acid strains other than *Streptococcus thermophilus* and *Lactobacillus delbrueckii* subsp. *bulgaricus*, are included to give the finished product various properties, such as the property of promoting the equilibrium of the flora. As used herein, the term "yoghurt" encompasses set yoghurt, stirred yoghurt, drinking yoghurt, Petit Suisse, heat treated yoghurt, strained or Greek style yoghurt characterized by a high protein level and yoghurt-like products.

In particular, term "yoghurt" encompasses, but is not limited to, yoghurt as defined according to French and European regulations, e.g. coagulated dairy products obtained by lactic acid fermentation by means of specific thermophilic lactic acid bacteria only (i.e. *Lactobacillus delbrueckii* subsp. *bulgaricus* and *Streptococcus thermophilus*) which are cultured simultaneously and are found to be live in the final product in an amount of at least 10 million CFU (colony-forming unit)/g. Yoghurts may optionally contain added dairy raw materials (e.g. cream) or other ingredients such as sugar or sweetening agents, one or more flavouring(s), fruit, cereals, or nutritional substances, especially vitamins, minerals and fibers, as well as stabilizers and thickeners. Optionally the yoghurt meets the specifications for fermented milks and yoghurts of the AFNOR NF 04-600 standard and/or the codex StanA-IIa-1975 standard. In order to satisfy the AFNOR NF 04-600 standard, the product must not have been heated after fermentation and the dairy raw materials must represent a minimum of 70% (m/m) of the finished product.

In a further embodiment the present invention provides food, feed or pharmaceutical products comprising one or more bacteria of the species *Lactobacillus fermentum* with antifungal effects as described above and one or more of:

(a) least one further bacterium selected from one or more of the following genera *Lactococcus* spp., *Streptococcus* spp., *Lactobacillus* spp., *Leuconostoc* spp., *Pseudoleuconostoc* spp., *Pedioccccus* spp., *Brevibacterium* spp. and *Enterococcus* spp;

(b) *Lactobacillus rhamnosus* bacterium of strain CHCC15860 as deposited with the German Collection of Microorganisms and Cell Cultures (DSMZ) under accession No. DSM32092;

(c) *Lactobacillus rhamnosus* bacterium of strain CHCC5366 as deposited with the German Collection of Microorganisms and Cell Cultures (DSMZ) under accession No. DSM23035;

(d) *Lactobacillus rhamnosus* bacterium of strain CHCC12697 as deposited with the German Collection of Microorganisms and Cell Cultures (DSMZ) under accession No. DSM24616;

(e) *Lactobacillus paracasei* bacterium of strain CHCC12777 as deposited with the German Collection of Microorganisms and Cell Cultures (DSMZ) under accession No. DSM24651; and (f) *Lactobacillus paracasei* bacterium of strain CHCC14676 as deposited with the German Collection of Microorganisms and Cell Cultures (DSMZ) under accession No. DSM25612.

EXAMPLE 1

Figure 1:
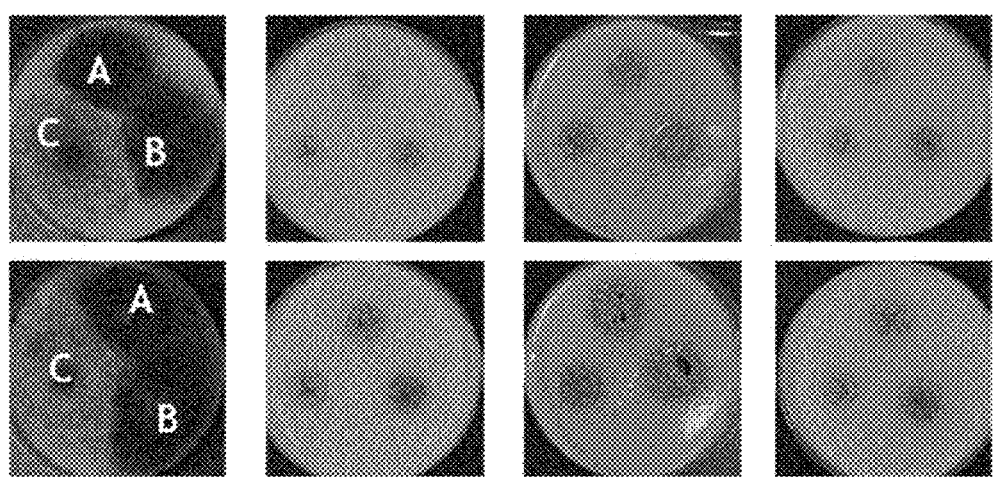
FIG. 1: Growth of molds on plates prepared from milk fermented with a starter culture alone (reference, first column), together with FreshQ®4 (second column), together with Holdbac® YM-C Plus (third column) or together with *Lb. fermentum* CHCC14591 (fourth column). The plates had been incubated at 7±1° C. for 19 days (top row) and 27 days (bottom row). The target contaminants were added in concentrations of 500 spores/spot: (A) *P. carneum*, (B) *P. paneum* and (C) *P. roqueforti*.
Figure 2:
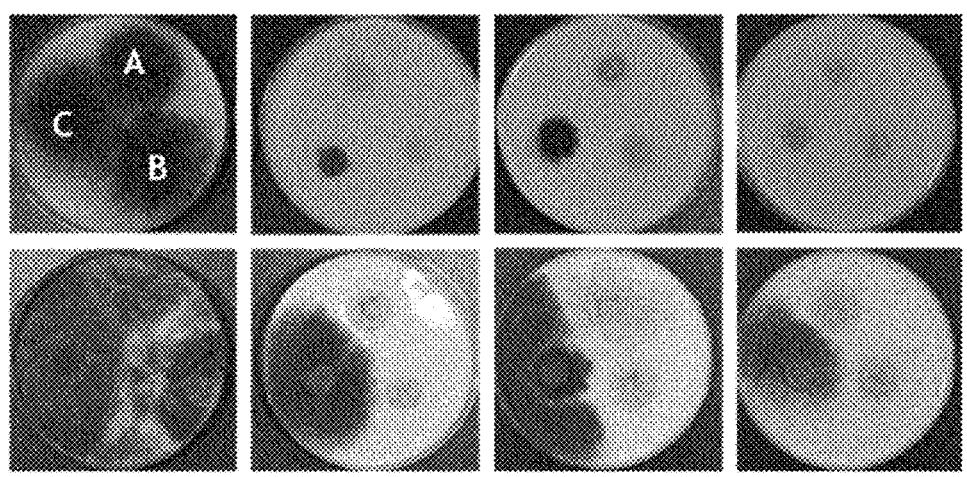
FIG. 2: Growth of molds on plates prepared from milk fermented with a starter culture alone (reference, first column), together with FreshQ®4 (second column), together with Holdbac® YM-C Plus (third column) or together with *Lb. fermentum* CHCC14591 (fourth column). The plates had been incubated at 25±1° C. for 6 days (top row) and 11 days (bottom row). The target contaminants were added in concentrations of 500 spores/spot: (A) *P. carneum,* (B) *P. paneum* and (C) *P. roqueforti*.

Semi-Quantitative Analysis of the Inhibitory Effect of Lb. Fermentum CHCC14591 against Different Yeast and Mold Contaminants and Diacetyl Production For the semi-quantitative analysis of the inhibitory effect of Lb. fermentum CHCC14591, an agar-assay was used, resembling the manufacturing process and product of yoghurt:

Reduced-fat (1.5% w/v) homogenized milk was heat-treated at 90±1° C. for 20 min and cooled immediately. A commercial starter culture (F-DVS Mild 2.0) was inoculated at 0.02% (v/w), and the inoculated milk was distributed into 200 ml bottles. One bottle was inoculated with Lb. fermentum CHCC14591 in total concentration of $2 \times 10^7$ CFU/g, two bottles were inoculated with either of two commercial bioprotective cultures (FreshQ®4 and Holdbac® YM-C Plus) in recommended dosages (100 U/T and 20 DCU/100 L for FreshQ®4 and Holdbac® YM-C Plus, respectively), and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

Spore suspension of six different molds were spotted in concentration of 500 spores/spot; *Penicillium brevicompactum* (DSM32094), *P. crustosum, P. solitum* (DSM32093), *P. carneum, P. paneum* and *P. roqueforti*. Three molds were spotted on each plate. Four yeasts including *Torulaspora delbrueckii, Cryptococcus hansenii, Debaryomyces hansenii* and *Yarrowia lipolytica* were spotted in concentrations of $10^4$, $10^3$ and $10^2$ CFU/spot. Plates were incubated at 7±1° C. and 25±1° C. and regularly examined for the growth of molds and yeast.

On day 14 samples were analysed for diacetyl by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

HS-autosampler: HS40XI, TurboMatrix 110, Perkin Elmer.
HS-software: HSControl v.2.00, Perkin Elmer.
GC: Autosystem XL, Perkin Elmer.
GC-software: Turbochrom navigator, Perkin Elmer.
Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

Figure 3:
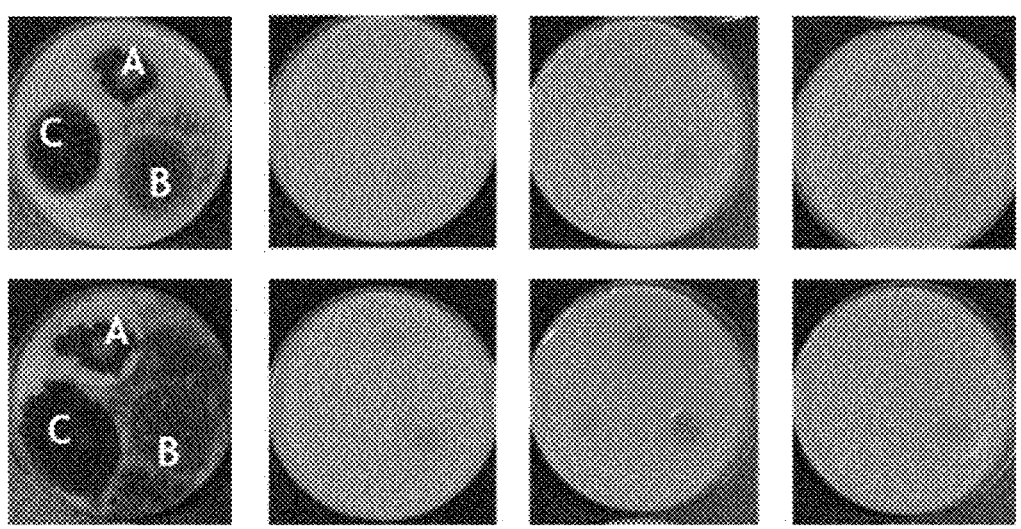
FIG. 3: Growth of molds an plates prepared from milk fermented with a starter culture alone (reference, first column), together with FreshQ®4 (second column), together with Holdbac® YM-C Plus (third column) or together with *Lb. fermentum* CHCC14591 (fourth column). The plates had been incubated at 7±1° C. for 19 days (top row) and 27 days (bottom row). The target contaminants were added in concentrations of 500 spores/spot: (A) *P. brevicompactum,* (B) *P. crustosum* and (C) *P. solitum*.
Figure 4:
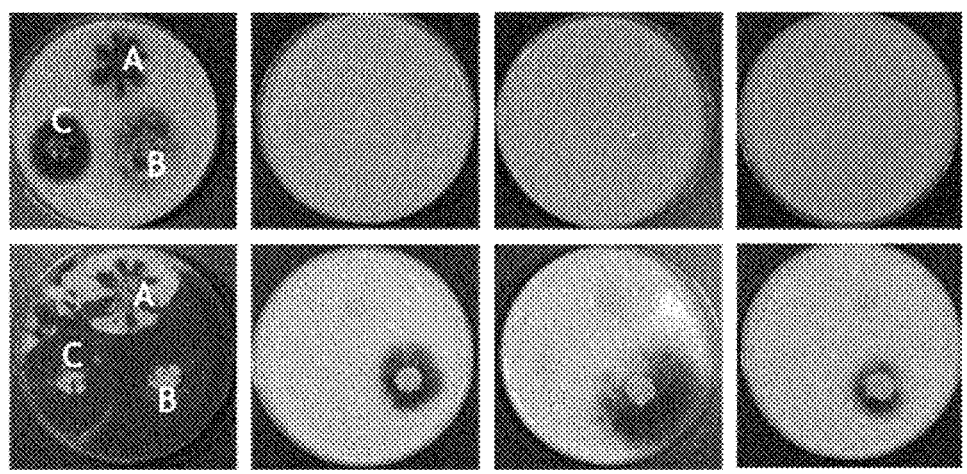
FIG. 4: Growth of molds on plates prepared from milk fermented with a starter culture alone (reference, first column), together with FreshQ®4 (second column), together with Holdbac® YM-C Plus (third column) or together with *Lb. fermentum* CHCC14591 (fourth column). The plates had been incubated at 25±1° C. for 6 days (top row) and 11 days (bottom row). The target contaminants were added in concentrations of 500 spores/spot: (A) *P. brevicompactum* (DSM32093), (B) *P. crustosum* and (C) *P. solitum* (DSM32093).
Figure 5:
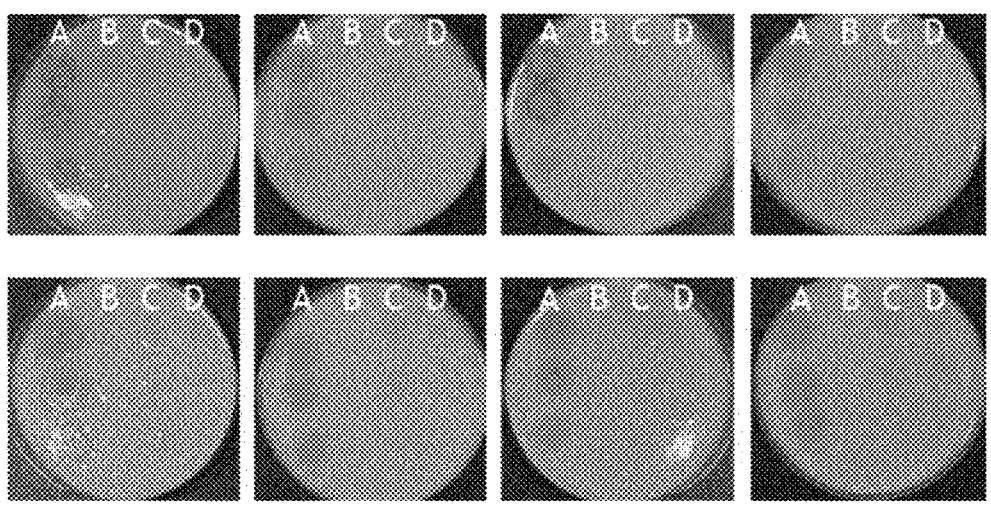
FIG. 5: Growth of yeast on plates prepared from milk fermented with a starter culture alone (reference, first column), together with FreshQ®4 (second column), together with Holdbac® YM-C Plus (third column) or together with *Lb. fermentum* CHCC14591 (fourth column). The plates had been incubated at 7±1° C. for 11 days (Top row) or at 25±1° C. for 5 days (bottom row). The target contaminants were added in concentrations of $1\times10^3$ cfu/spot (top row), $1\times10^2$ cfu/spot (middle row) and $1\times10^3$ cfu/spot (bottom row): (A) *Torulaspora delbrueckii*, (B) *Cryptococcus hansenii*, (C) *Debaryomyces hansenii* and (D) *Yarrowia lipolytica*.

Results of the agar-assay are presented in FIGS. 1-5, showing that all of the tested molds grew very well on the agar plates made from milk fermented only with the starter culture (reference). However, when *Lb. fermentum* CHCC14591 was present during milk fermentation the resulting plates inhibited growth of all of the *Penicillium* species tested. The level of inhibition was comparable or even higher than the inhibition observed for the two commercial bioprotective cultures. FIG. 3 shows that all of the tested yeasts grew on the agar plates made from milk fermented only with the starter culture (reference). When *Lb. fermentum* CHCC14591 was present during milk fermentation the resulting plates prevented growth of *C. fragiola* and *Y. lipolytica* added in all concentrations. Growth of *T. delbrueckii* and *D. hansenii* was inhibited in the lower concentrations when *Lb. fermentum* CHCC14591 was present during milk fermentation. The level of inhibition was comparable or even higher than the inhibition observed for the two commercial bioprotective cultures.

Figure 6:
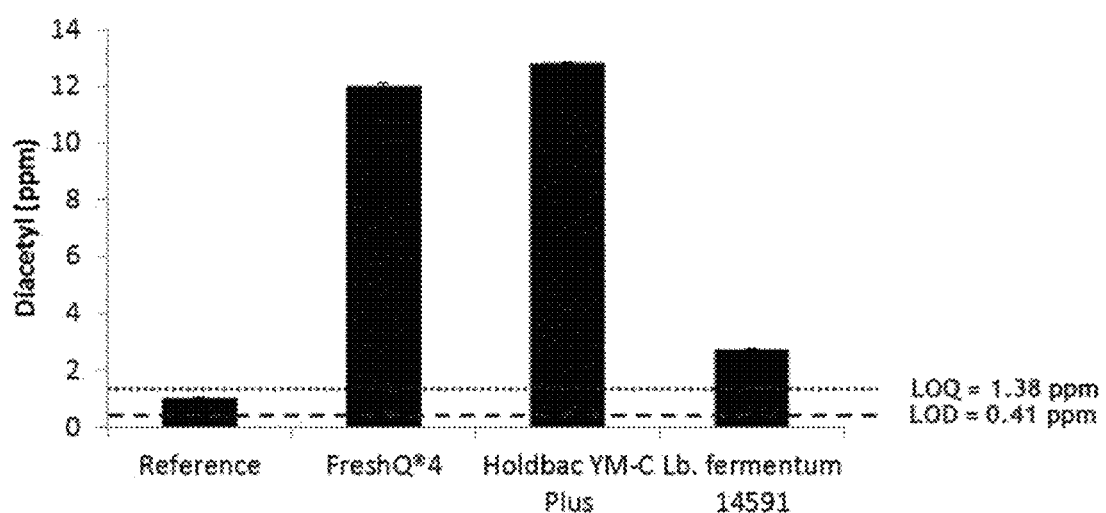
FIG. 6: Diacetyl levels after storage at 7±1° C. for 14 days in fermented milk products fermented with starter culture alone (Reference), or starter cultures in combination with FreshQ®4, Holdbac® YM-C Plus or *Lb. fermentum* CHCC14591. LOD: Limit of detection. LOQ: Limit of quantification.

The effect on diacetyl production is illustrated in FIG. 6, showing that addition of *Lb. fermentum* CHCC14591 during milk fermentation produce minimal amounts of diacetyl when compared to commercially available alternatives.

EXAMPLE 2

Semi-Quantitative Analysis of the Inhibitory Effect of *Lb. Fermentum* CHCC14591 in Combination with *Lb. Rhamnosus* CHCC15860 against Different Mold Contaminants For the semi-quantitative analysis of the inhibitory effect of a combination of *Lb. fermentum* CHCC14591 and *Lb. rhamnosus* CHCC15860, an agar-assay was used, resembling the manufacturing process and product of yoghurt:

Reduced-fat (1.5% w/v) homogenized milk was heat-treated at 90±1° C. for 20 min and cooled immediately. A commercial starter culture (F-DVS Mild 2.0) was inoculated at 0.02% (v/w), and the inoculated milk was distributed into 200 ml bottles. One bottle was inoculated with *Lb. rhamnosus* CHCC15860 in total concentration of $1×10^7$ CFU/g, one bottle was inoculated with *Lb. fermentum* CHCC14591 in total concentration of $1×10^7$ CFU/g, one bottle was inoculated with *Lb. fermentum* CHCC14591 and *Lb. rhamnosus* CHCC15860 each in concentration of $5×10^6$ CFU/g, and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

Spore suspension of three different molds were spotted in concentration of 500 spores/spot; *P. carneum, P. paneum* and *P. roqueforti*. Three molds were spotted on each plate. Plates were incubated at 25±1° C. and regularly examined for the growth of molds.

Figure 7:
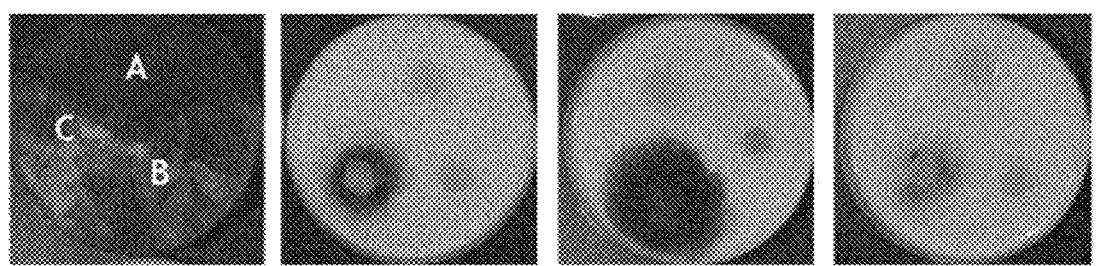
FIG. 7: Growth of molds on plates prepared from milk fermented with a starter culture alone (reference, first column), together *Lb. rhamnosus* CHCC15860 (second column), together with *Lb. fermentum* CHCC14591 (third column) or together with a combination of *Lb. rhamnosus* CHCC15860 and *Lb. fermentum* CHCC14591 (fourth column). The plates had been incubated at 25±1° C. for 5 days. The target contaminants were added in concentrations of 500 spores/spot: (A) *P. carneum,* (B) *P. paneum* and (C) *P. roqueforti*.

Results of the agar-assay are presented in FIG. 7, showing that all of the tested molds grew very well on the agar plates made from milk fermented only with the starter culture (reference). However, when *Lb. rhamnosus* 15860 or the *Lb. fermentum* CHCC14591 were present during milk fermentation the resulting plates inhibited growth of the three *Penicillium* species tested. Furthermore, a synergistic inhibitory effect was found when *Lb. rhamnosus* CHCC15860 and *Lb. fermentum* CHCC14591 were used in combination compared to the inhibitory effect of each strain used alone.

EXAMPLE 3

A Semi-Quantitative Analysis of the Inhibitory Effect of Ten *Lb. Fermentum* Strains against Different Mold Contaminants For the semi-quantitative analysis of the inhibitory effect of ten *Lb. fermentum* strains, an agar-assay was used, resembling the manufacturing process and product of yoghurt:

Reduced-fat (1.5% w/v) homogenized milk was heat-treated at 90±1° C. for 20 min and cooled immediately. A commercial starter culture (F-DVS YF-L901) was inoculated at 0.02% (v/w), and the inoculated milk was distributed into 200 ml bottles. Ten bottles were inoculated with the *Lb. fermentum* strains in concentrations of $1×10^7$ CFU/g and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

The tested Lb. fermentum strains were: Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15848, Lb. fermentum CHCC15926, and Lb. fermentum CHCC2008.

Spore suspension of six different molds were spotted in concentration of 500 spores/spot; Penicillium brevicompactum (DSM32094), P. crustosum, P. solitum (DSM32093), P. carneum, P. paneum and P. roqueforti. Three molds were spotted on each plate. Plates were incubated at 25±1° C. and regularly examined for the growth of molds.

On day 14 samples were analysed for diacetyl by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

HS-autosampler: HS40XI, TurboMatrix 110, Perkin Elmer.
HS-software: HSControl v.2.00, Perkin Elmer.
GC: Autosystem XL, Perkin Elmer.
GC-software: Turbochrom navigator, Perkin Elmer.
Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

To monitor the effect on post acidification, the eleven fermented milk samples (starter culture alone and starter culture in combination with the ten Lb. fermentum strains) were stored at 7±1° C. and 25±1° C. for 28 days and pH was measured on day 1, 7, 14, 21 and 28.

Figure 8:
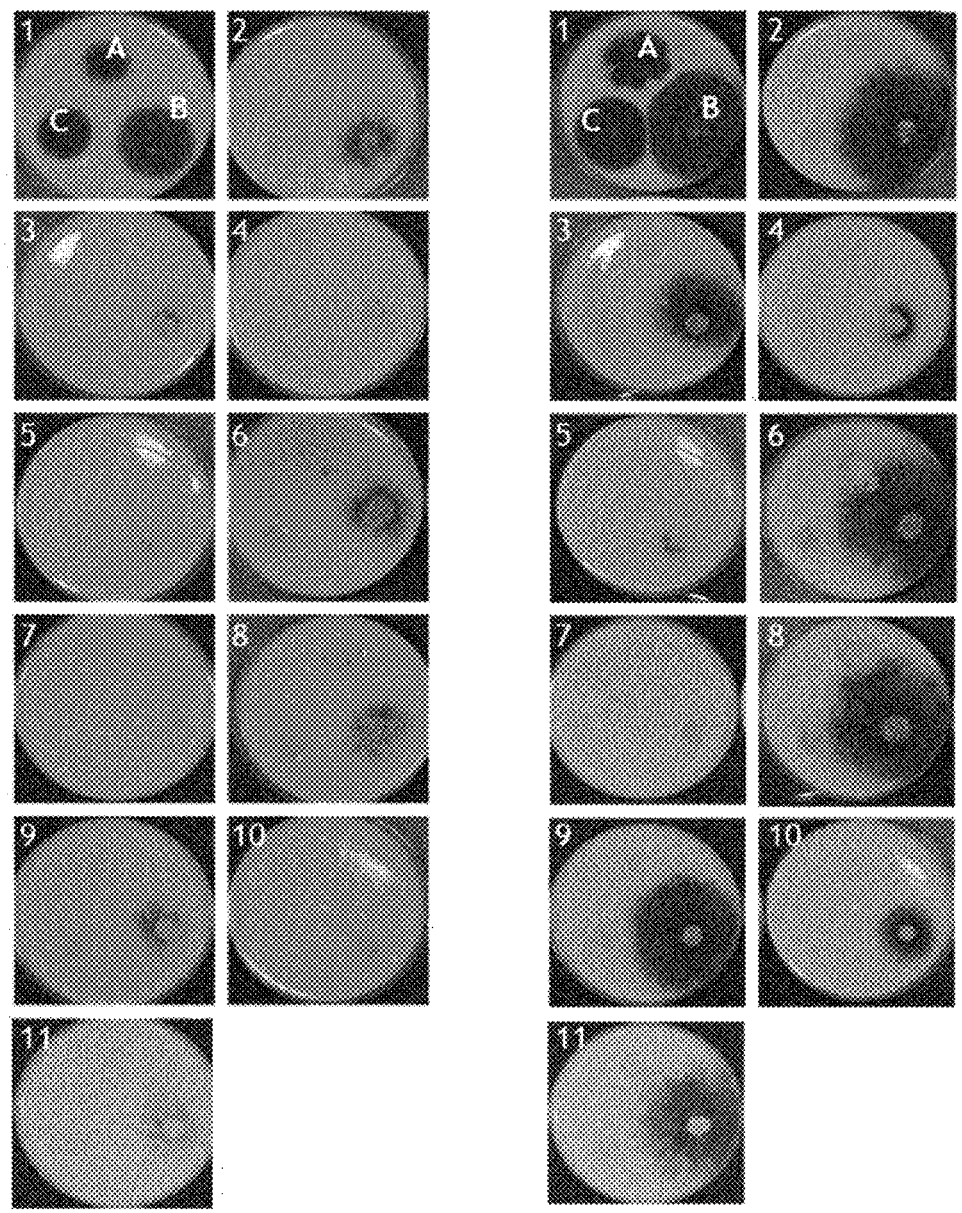
FIG. 8: Growth of molds on plates prepared from milk fermented with (1) a starter culture alone, together with (2) Lb. fermentum CHCC12798, (3) Lb. fermentum CHCC12797, (4) Lb. fermentum CHCC14591, (5) Lb. fermentum CHCC14588, (6) Lb. fermentum CHCC15844, (7) Lb. fermentum CHCC15865, (8) Lb. fermentum CHCC15847, (9) Lb. fermentum CHCC15848, (10) Lb. fermentum CHCC15926, and (11) Lb. fermentum CHCC2008. The plates had been incubated at 25±1° C. for 5 days (left column of photos) or 7 days (right column of photos). The target contaminants were added in concentrations of 500 spores/spot: (A) P. brevicompactum (DSM32094), (B) P. crustosum and (C) P. solitum (DSM32093).

Results of the agar-assay are presented in FIG. 8, showing that all of the tested molds grew very well on the agar plates made from milk fermented only with the starter culture (reference). For P. brevicompactum (DSM32094) and P. solitum (DSM32093) a large delay in the growth was observed for all of the Lb. fermentum strains when present during milk fermentation. For the remaining molds tested a varying delay in the growth was observed when the Lb. fermentum strains were present during milk fermentation. Bacteria of the strain Lb. fermentum CHCC14591 achieved significant inhibition of essentially all molds tested in this assay.

Figure 9:
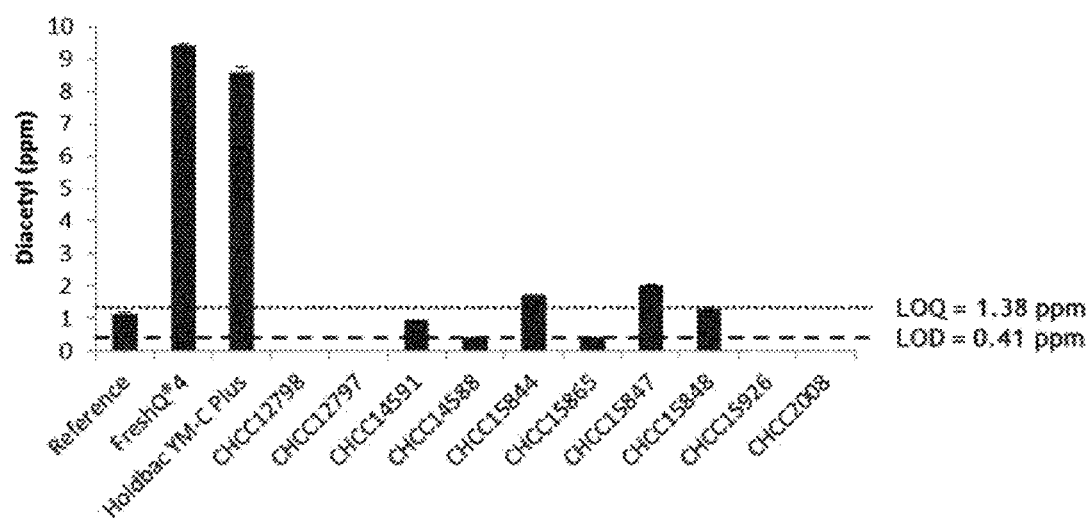
FIG. 9: Diacetyl levels after storage at 7±1° C. for 14 days in fermented milk products fermented with starter culture alone (Reference), or starter cultures in combination with FreshQ®4, Holdbac® YM-C Plus or Lb. fermentum strains. LOD: Limit of detection. LOQ: Limit of quantification.

The effect on diacetyl production is illustrated in FIG. 9, showing that each of the anti-fungal strains Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15848, Lb. fermentum CHCC15926 and Lb. fermentum CHCC2008 secretes either none or very little diacetyl.

Figure 10:
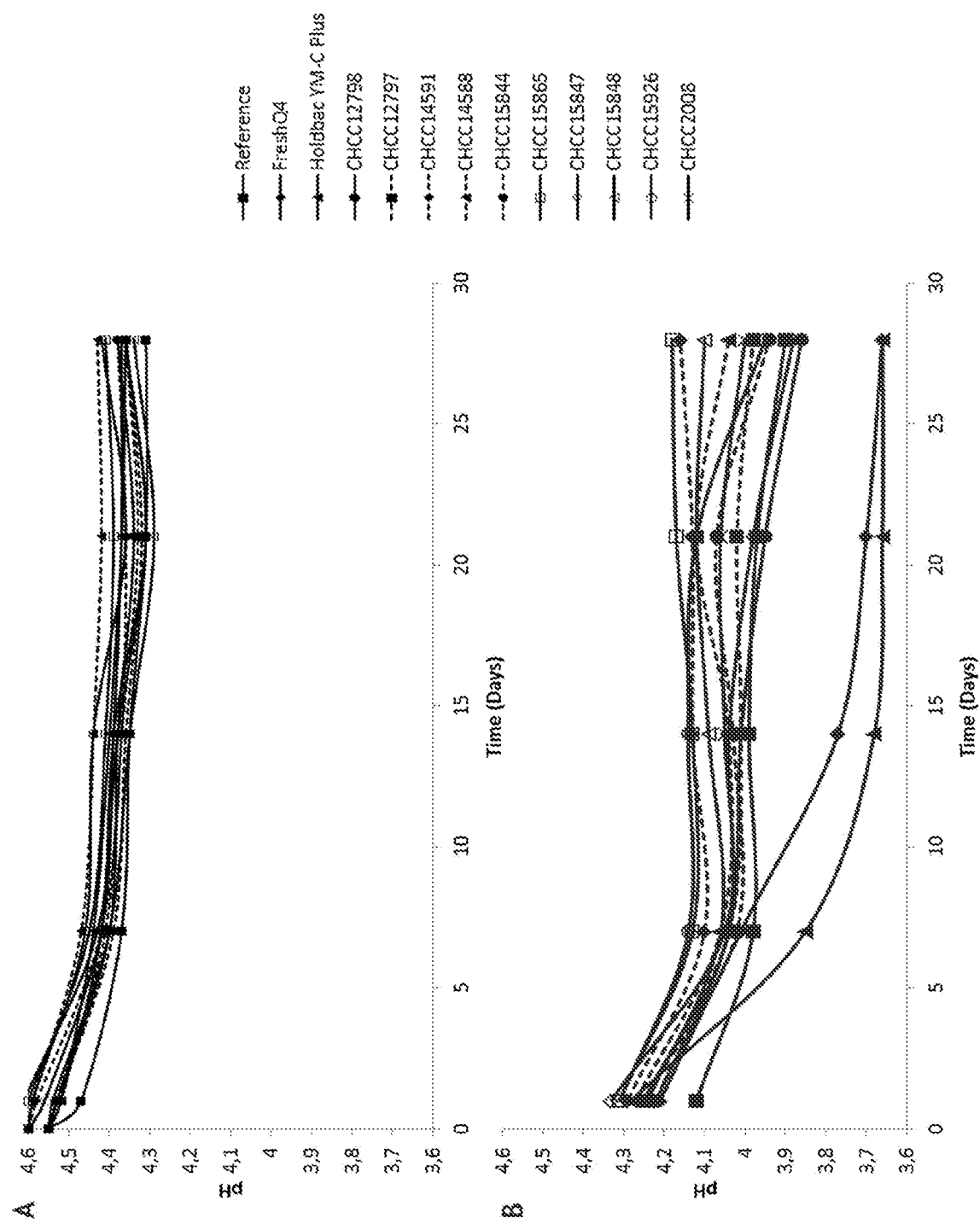
FIG. 10: pH development in fermented milk products over time when stored at (A) 7±1° C. and (B) 25±1° C. for 28 days. The products are fermented with starter culture only, Reference, or starter culture in combination with FreshQ®4, Holdbac®® YM-C Plus or Lb. fermentum strains.

The effects on post-acidification are illustrated in FIG. 10 and show that each of the Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15848, Lb. fermentum CHCC15926, and Lb. fermentum CHCC2008 does not contribute to post-acidification or even reduce post-acidification compared to reference yoghurt.

These findings were unexpected and are highly significant, as prior art antifungal food-grade bacteria were observed to contribute to the secretion of volatile compounds and to increase the post-acidification effects caused by the starter culture.

EXAMPLE 4

Effect of One Lb. Fermentum Strain on Post-Acidification

One Lb. fermentum strain (CHCC14591) was tested for the effect on post-acidification.

Reduced-fat (1.5% w/v) homogenized milk was heat-treated at 90±1° C. for 20 min and cooled immediately. A commercial starter culture (F-DVS Mild 2.0) was inoculated at 0.02% (v/w), and the inoculated milk was distributed into 200 ml bottles. One bottle was inoculated with Lb. fermentum CHCC14591 in total concentration of $2 \times 10^7$ CFU/g, two bottles were inoculated with either of two commercial bioprotective cultures (FreshQ®4 and Holdbac® YM-C Plus) in recommended dosages (100 U/T and 20 DCU/100 L for FreshQ®4 and Holdbac® YM-C Plus, respectively), and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice.

To monitor the effect on post acidification, the four fermented milk samples (starter-only, FreshQ®4, Holdbac® YM-C Plus and Lb. fermentum CHCC14591) were stored at 7±1° C. and 25±1° C. for 21 days and pH was measured on day 1, 7, 14 and 21.

Figure 11:
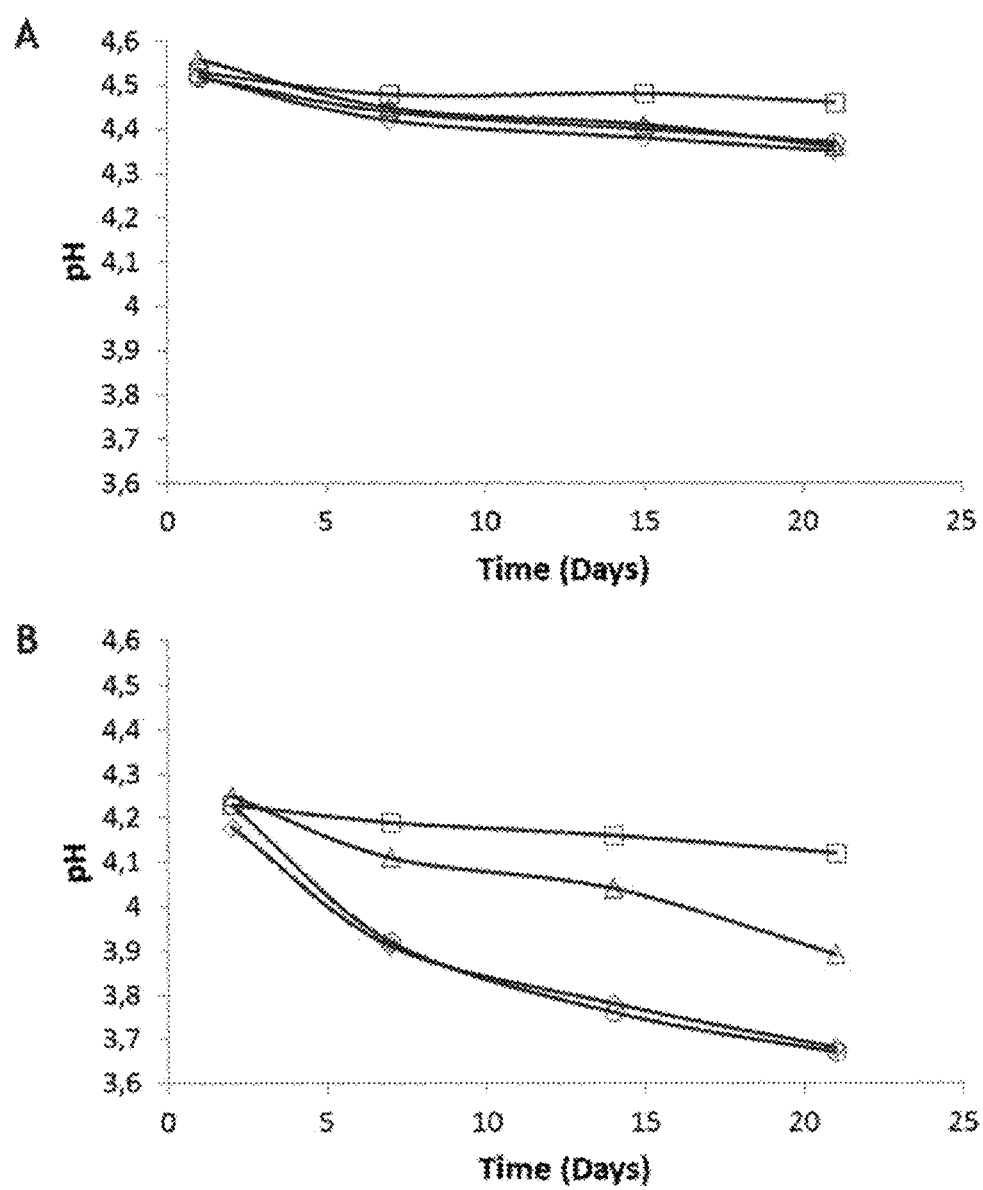
FIG. 11: pH development in fermented milk products over time when stored at (A) 7±1° C. or (B) 25±1° C. for 21 days. The products are fermented with starter culture only (Reference, Δ) or starter culture in combination with FreshQ®4 (◇), Holdbac® YM-C Plus (○) or Lb. fermentum CHCC14591 (□).

The effect on post-acidification is illustrated in FIG. 11, showing that addition of Lb. fermentum CHCC14591 during milk fermentation prevents post-acidification of the fermented milk product. The starter culture alone gives slight post-acidification and the two commercial bioprotective cultures both contribute to post-acidification.

EXAMPLE 5

Effect of the Ten Lb. Fermentum Stains of Acetaldehyde Content

Ten Lb. fermentum strains were tested for their ability to lower acetaldehyde content.

Reduced-fat (1.5% w/v) homogenized milk was heat-treated at 90±1° C. for 20 min and cooled immediately. A commercial starter culture (F-DVS YF-L901 Yo-Flex®) was inoculated at 0.02% (v/w), and the inoculated milk was distributed into 200 ml bottles. Ten bottles were inoculated with the Lb. fermentum strains in concentrations of $1 \times 10^7$ CFU/g and one bottle was used as a reference and only inoculated with the starter culture. All bottles were incubated in a water bath at 43±1° C. and fermented at these conditions until pH of 4.60±0.1 was reached. After fermentation, the bottles were vigorously shaken to break the coagulum and cooled on ice. The bottles were stored at 7±1° C. for 14 days.

On day 14 samples were analyzed for acetaldehyde by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:
  HS-autosampler: HS40XI, TurboMatrix 110, Perkin Elmer.
  HS-software: HSControl v.2.00, Perkin Elmer.
  GC: Autosystem XL, Perkin Elmer.
  GC-software: Turbochrom navigator, Perkin Elmer.
  Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

Figure 12:
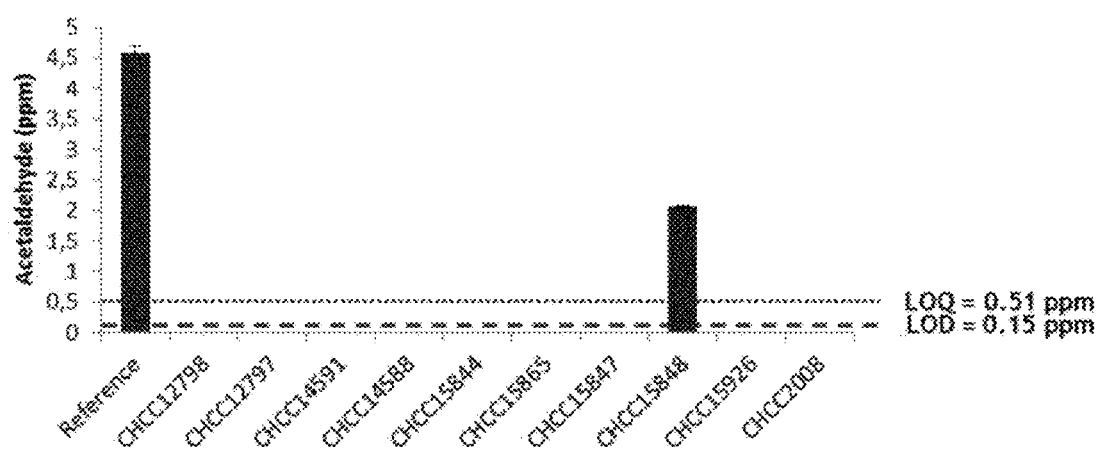
FIG. 12: Acetaldehyde levels after storage at 7±1° C. for 14 days in fermented milk products fermented with starter culture alone (Reference), or starter cultures in combination with Lb. fermentum strains. LOD: Limit of detection. LOQ: Limit of quantification.

The results are illustrated in FIG. 12 and show that each of the strains *Lb. fermentum* CHCC12798, *Lb. fermentum* CHCC12797, *Lb. fermentum* CHCC14591, *Lb. fermentum* CHCC14588, *Lb. fermentum* CHCC15844, *Lb. fermentum* CHCC15865, *Lb. fermentum* CHCC15847, *Lb. fermentum* CHCC15848, *Lb. fermentum* CHCC15926, and *Lb. fermentum* CHCC2008 has the ability to reduce the concentration of acetaldehyde produced by a starter culture during fermentation in a fermented milk product.

EXAMPLE 6

Effect of One *Lb. Fermentum* Strain on Acetaldehyde Content

One *Lb. fermentum* strain was tested for the ability to lower acetaldehyde content.

Reduced-fat (1.5% w/v) homogenized milk was heat-treated at 90±1° C. for 20 min and cooled immediately. A commercial starter culture (F-DVS Mild 2.0) was inoculated at 0.02% (v/w), and the inoculated milk was distributed into two 200 ml bottles. One bottle was inoculated with the *Lb. fermentum* strains in concentrations of 1×10$^7$ CFU/g and one bottle was used as a reference and only inoculated with the starter culture. Both bottles were incubated in a water bath at 43±1° C. and fermented at these conditions until pH of 4.60±0.1 was reached. After fermentation, the bottles were vigorously shaken to break the coagulum and cooled on ice. The bottles were stored at 7±1° C. for 14 days.

On day 14 samples were analyzed for acetaldehyde by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:
  HS-autosampler: HS40XI, TurboMatrix 110, Perkin Elmer.
  HS-software: HSControl v.2.00, Perkin Elmer.
  GC: Autosystem XL, Perkin Elmer.
  GC-software: Turbochrom navigator, Perkin Elmer.
  Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

Figure 13:
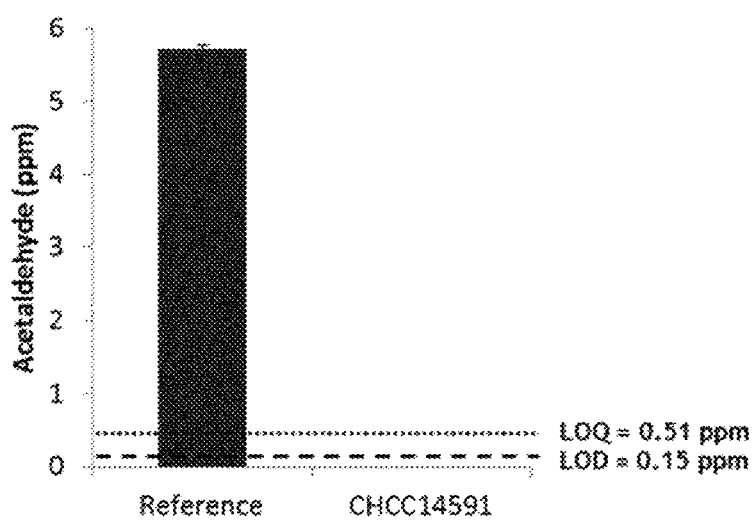
FIG. 13: Acetaldehyde levels after storage at 7±1° C. for 14 days in fermented milk products fermented with starter culture alone (Reference), or starter cultures in combination with Lb. fermentum CHCC14591. LOD: Limit of detection. LOQ: Limit of quantification.

The results are illustrated in FIG. 13 and show that *Lb. fermentum* CHCC14591 has the ability to reduce the concentration of acetaldehyde produced by a starter culture during fermentation in a fermented milk product.

EXAMPLE 7

Functional Analysis of Commercial Starter Starter Cultures

The four commercial starter cultures included herein were chosen based on their different acidification profiles. Three were frozen, F-DVS CH-1, F-DVS YoFlex Mild 2.0 and F-DVS YF-L901, and one was freeze dried, FD-DVS YF-L812. To test the difference in acidification profiles, semi fat milk was standardized to 1% fat and 4.5% protein with skim milk powder and heat-treated at 85±1° C. for 30 min and cooled immediately. One of four different commercial starter cultures (F-DVS CH-1, F-DVS YoFlex Mild 2.0, F-DVS YF-L901 or FD-DVS YF-L812) was inoculated at 0.02% (v/w), and the inoculated milk was distributed into 200 ml bottles. The bottles were incubated in a water bath at 43±1° C. and fermented under these conditions until pH 4.5 was reached. The pH was measured continually throughout the fermentation. Subsequently, the bottles were stored at 6° C. for 43 for days and pH was measured with intervals of 7 days to determine the level of post-acidification.

Figure 14:
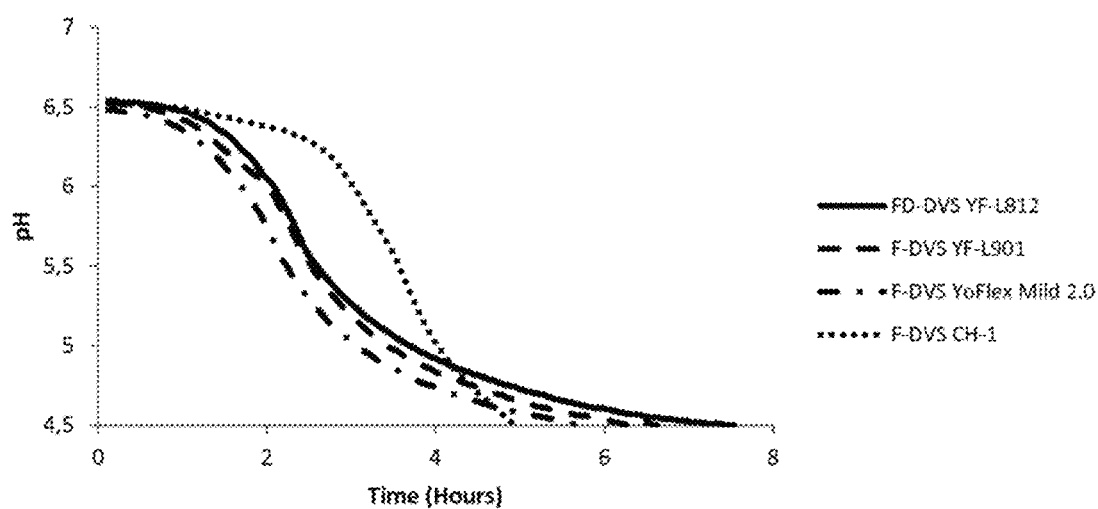
FIG. 14: Acidification curves of four commercial starter cultures, FD-DVS YF-L812, F-DVS YF-L901, F-DVS YoFlex Mild 2.0 and F-DVS CH-1, grown in milk (1% fat and 4.5% protein) at 43° C.
Figure 15:
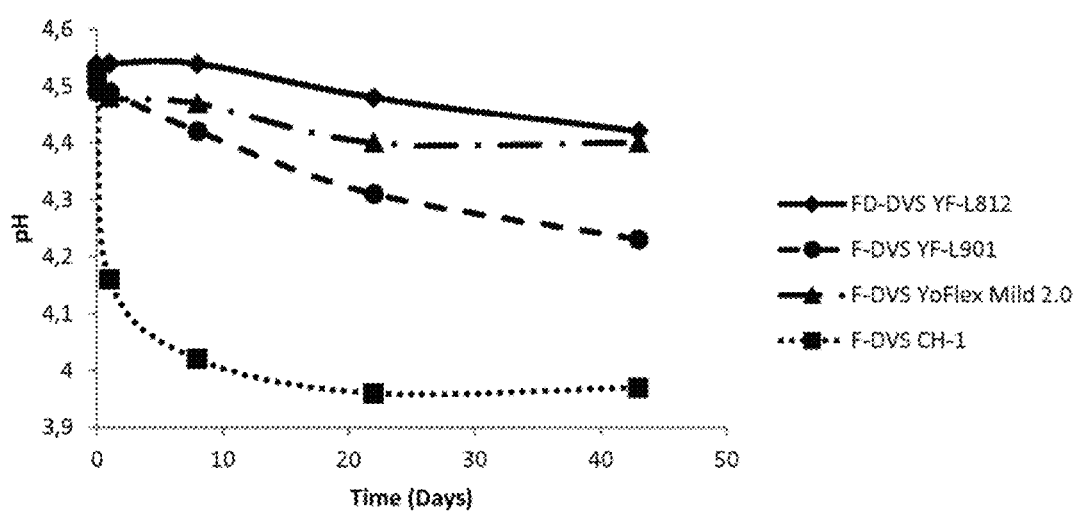
FIG. 15: Post-acidification curves of yoghurt fermented with one of four commercial starter cultures, FD-DVS YF-L812, F-DVS YF-L901, F-DVS YoFlex Mild 2.0 and F-DVS CH-1 after storage at 6° C. for up to 43 days.
Figure 16:
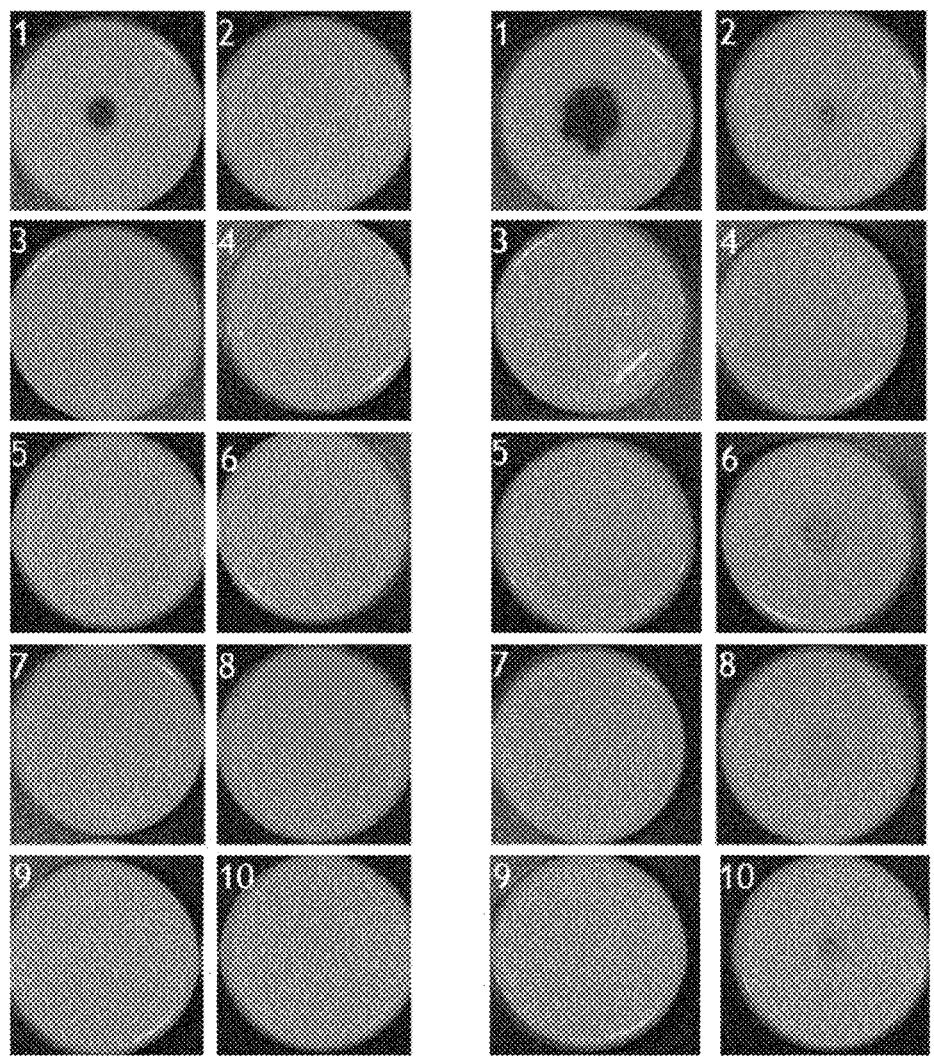
FIG. 16: Growth of molds on plates prepared from milk fermented with (1) a starter culture alone, FD-DVS YF-L812, together with (2) Lb. fermentum CHCC12798, (3) Lb. fermentum CHCC12797, (4) Lb. fermentum CHCC14591, (5) Lb. fermentum CHCC14588, (6) Lb. fermentum CHCC15844, (7) Lb. fermentum CHCC15865, (8) Lb. fermentum CHCC15847, (9) Lb. fermentum CHCC15926, and (10) Lb. fermentum CHCC2008. The plates had been incubated at 25±1° C. for 4 days (left column of photos) or 8 days (right column of photos). The target contaminant, P. brevicompactum (DSM32094), was added in concentrations of 500 spores/spot.
Figure 17:
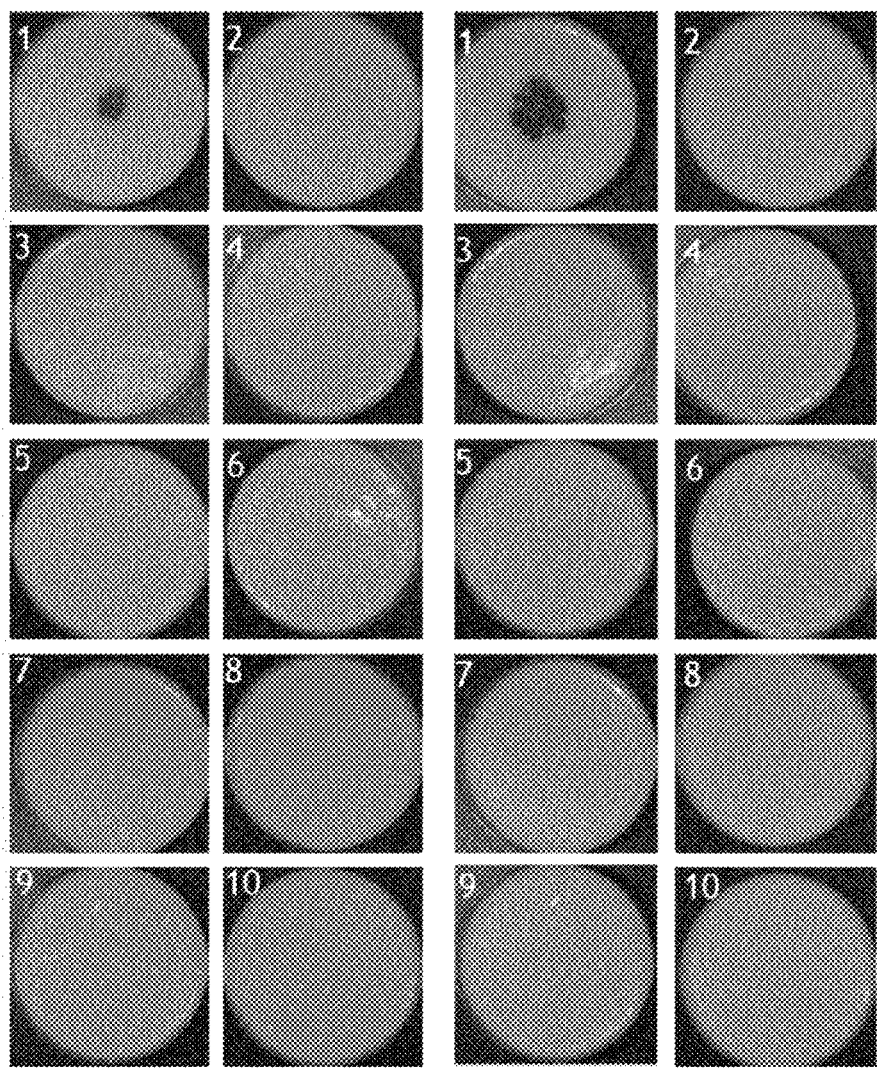
FIG. 17: Growth of molds on plates prepared from milk fermented with (1) a starter culture alone, F-DVS CH-1, together with (2) Lb. fermentum CHCC12798, (3) Lb. fermentum CHCC12797, (4) Lb. fermentum CHCC14591, (5) Lb. fermentum CHCC14588, (6) Lb. fermentum CHCC15844, (7) Lb. fermentum CHCC15865, (8) Lb. fermentum CHCC15847, (9) Lb. fermentum CHCC15926, and (10) Lb. fermentum CHCC2008. The plates had been incubated at 25±1° C. for 4 days (left column of photos) or 8 days (right column of photos). The target contaminant, P. brevicompactum (DSM32094), was added in concentrations of 500 spores/spot.
Figure 18:
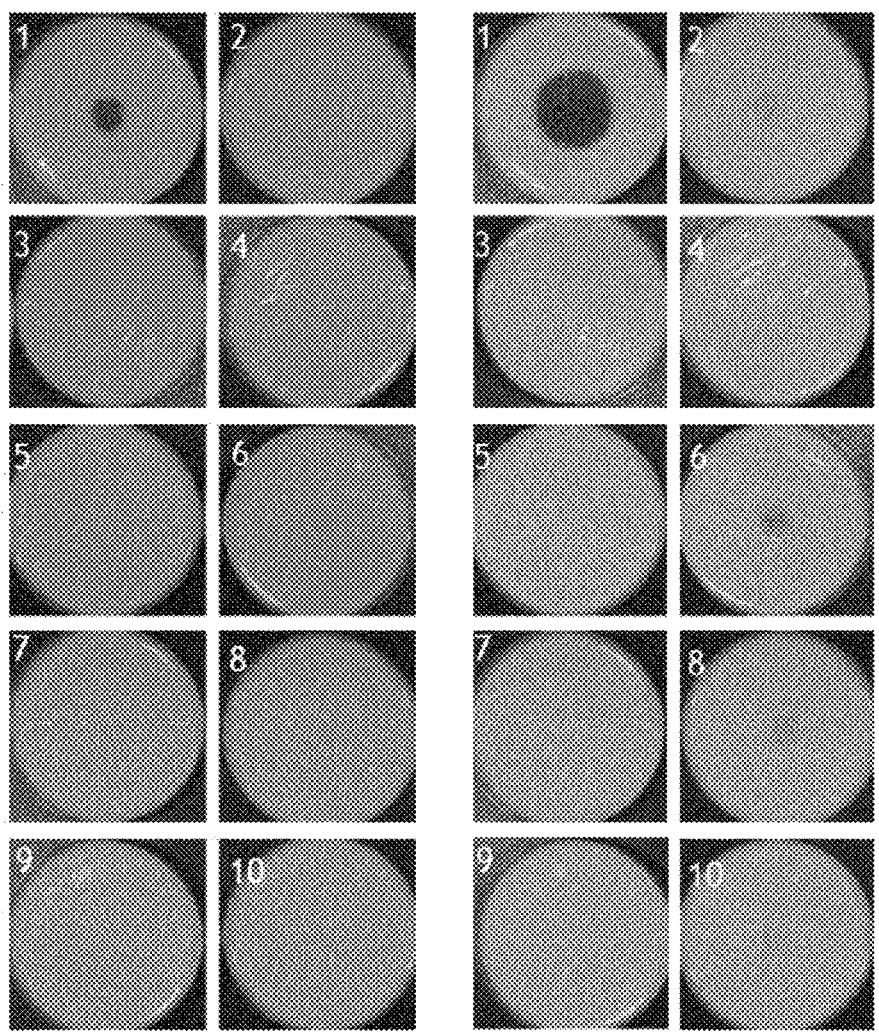
FIG. 18: Growth of molds on plates prepared from milk fermented with (1) a starter culture alone, FD-DVS YF-L812, together with (2) Lb. fermentum CHCC12798, (3) Lb. fermentum CHCC12797, (4) Lb. fermentum CHCC14591, (5) Lb. fermentum CHCC14588, (6) Lb. fermentum CHCC15844, (7) Lb. fermentum CHCC15865, (8) Lb. fermentum CHCC15847, (9) Lb. fermentum CHCC15926, and (10) Lb. fermentum CHCC2008. The plates had been incubated at 25±1° C. for 4 days (left column of photos) or 8 days (right column of photos). The target contaminant, P. solitum (DSM32093), was added in concentrations of 500 spores/spot.
Figure 19:
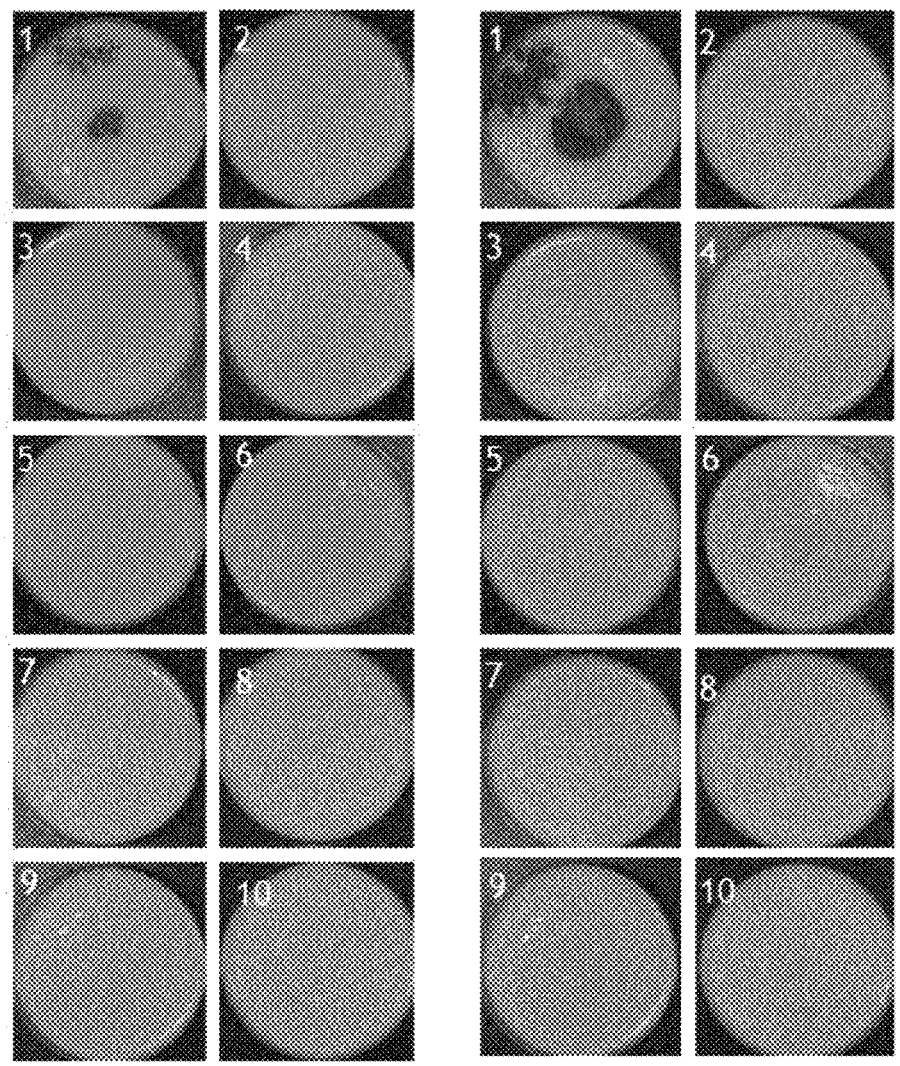
FIG. 19: Growth of molds on plates prepared from milk fermented with (1) a starter culture alone, F-DVS CH-1, together with (2) Lb. fermentum CHCC12798, (3) Lb. fermentum CHCC12797, (4) Lb. fermentum CHCC14591, (5) Lb. fermentum CHCC14588, (6) Lb. fermentum CHCC15844, (7) Lb. fermentum CHCC15865, (8) Lb. fermentum CHCC15847, (9) Lb. fermentum CHCC15926, and (10) Lb. fermentum CHCC2008. The plates had been incubated at 25±1° C. for 4 days (left column of photos) or 8 days (right column of photos) The target contaminant, P. solitum (DSM32093), was added in concentrations of 500 spores/spot.

The acidification profiles of the four commercial starter cultures, F-DVS CH-1, F-DVS YoFlex Mild 2.0, F-DVS YF-L901 and FD-DVS YF-L812, are shown in FIG. 14. F-DVS CH-1 showed fast fermentation time reaching pH 4.55 in 4.87 hours. F-DVS YoFlex Mild 2.0 showed intermediate fermentation time reaching pH 4.55 in 5.29 hours. FD-DVS YF-L812 and F-DVS YF-L901 showed slower fermentation reaching pH 4.55 in 6.45 and 5.87 hours, respectively. Post-acidification profiles showed very low levels of post-acidification for FD-DVS YF-L812 and F-DVS YoFlex Mild 2.0 (ΔpH=0.12 and ΔpH=0.11 after storage at 6° C. for 43 days), intermediate levels of post-acidification for F-DVS YF-L901 (ΔpH=0.26 after storage at 6° C. for 43 days and high degree of post-acidification for F-DVS CH-1 (ΔpH=0.55 after storage at 6° C. for 43 days) (FIG. 15).

EXAMPLE 8

Semi-Quantitative Analysis of the Inhibitory Effect of Nine *Lb. Fermentum* Strains against Different Mold Contaminants when Fermented with Two Different Starter Cultures For the semi-quantitative analysis of the inhibitory effect of nine *Lb. fermentum* strains, an agar-assay was used, resembling the manufacturing process and product of yoghurt:

Reduced-fat (1.5% w/v) homogenized milk was heat-treated at 90±1° C. for 20 min and cooled immediately. Milk was inoculated with one of two commercial starter cultures (F-DVS CH-1 or FD-DVS YF-L812) at 0.02% (v/w), and the inoculated milk was distributed into 200 ml bottles. Nine bottles inoculated with each starter culture were further inoculated with the Lb. fermentum strains in concentrations of $1\times10^7$ CFU/g and one bottle inoculated with each starter culture was used as a reference and only inoculated with the starter culture. All bottles were incubated in a water bath at 43±1° C. and fermented at these conditions until pH of 4.55±0.1 was reached. After fermentation, the bottles were vigorously shaken to break the coagulum and cooled on ice. Then the fermented milk was warmed to a temperature of 40° C. and added 40 ml of a 5% sterile agar solution that had been melted and cooled down to 60° C. This solution of fermented milk and agar was then poured into sterile Petri dishes and the plates were dried in a LAF bench for 30 min.

The tested Lb. fermentum strains were: Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15926, and Lb. fermentum CHCC2008.

Spore suspensions of two different molds were spotted in concentration of 500 spores/spot; Penicillium brevicompactum (DSM32094) and P. solitum (DSM32093). One mold was spotted on each plate. Plates were incubated at 7±1° C. and 25±1° C. and regularly examined for the growth of molds.

On day 14 samples were analysed for diacetyl by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

HS-autosampler: HS40XI, TurboMatrix 110, Perkin Elmer.
HS-software: HSControl v.2.00, Perkin Elmer.
GC: Autosystem XL, Perkin Elmer.
GC-software: Turbochrom navigator, Perkin Elmer.
Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

Results of the agar-assay are presented in FIGS. 16-19, showing that both of the tested molds grew very well on the agar plates made from milk fermented only with one of the starter cultures (reference). For both P. brevicompactum (DSM32094) and P. solitum (DSM32093) a large delay in the growth was observed for all of the Lb. fermentum strains, when present during milk fermentation regardless of the starter culture used.

Figure 20:
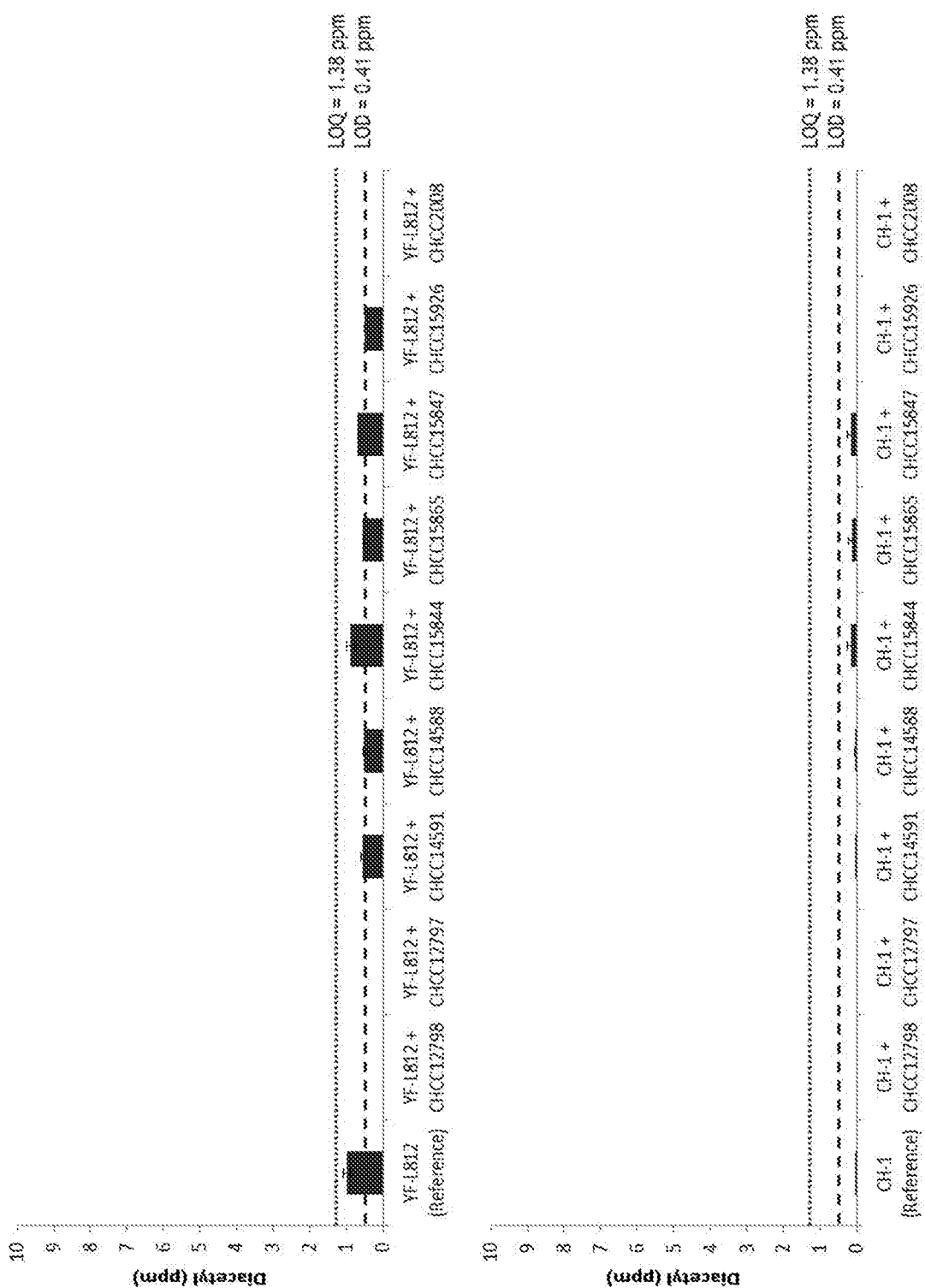
FIG. 20: Diacetyl levels after storage at 7±1° C. for 14 days in fermented milk products fermented with starter culture, FD DVS YF-L812 or F-DVS CH-1, alone (Reference), or starter cultures in combination one of the nine Lb. fermentum strains. LOD: limit of detection. LOQ: Limit of quantification.

The effect on diacetyl production is illustrated in FIG. 20, showing that each of the anti-fungal strains Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15926, and Lb. fermentum CHCC2008 adds no diacetyl to the level produced by the starter culture.

These findings were unexpected and are highly significant, as prior art antifungal food-grade bacteria were observed to contribute to the secretion of volatile compounds caused by the starter culture.

EXAMPLE 9

Effect of the Nine Lb. Fermentum Strains on Acetaldehyde Content when Fermented with Two Different Starter Cultures Nine Lb. fermentum strains were tested for their ability to lower acetaldehyde content.

Reduced-fat (1.5% w/v) homogenized milk was heat-treated at 90±1° C. for 20 min and cooled immediately. Milk was inoculated with one of two commercial starter cultures (F-DVS CH-1 or FD-DVS YF-L812) at 0.02% (v/w), and the inoculated milk was distributed into 200 ml bottles. Nine bottles were inoculated with the Lb. fermentum strains in concentrations of $1\times10^7$ CFU/g and one bottle inoculated with each starter culture was used as a reference and only inoculated with the starter culture. All bottles were incubated in a water bath at 43±1° C. and fermented at these conditions until pH of 4.55±0.1 was reached. After fermentation, the bottles were vigorously shaken to break the coagulum and cooled on ice. The bottles were stored at 7±1° C. for 14 days.

The tested Lb. fermentum strains were: Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15926, and Lb. fermentum CHCC2008.

On day 14 samples were analyzed for acetaldehyde by static head space gas chromatography (HSGC), a sensitive method for analyzing volatiles in complex matrices. The setup consisted of a Static Head Space sampler connected to Gas Chromatograph with Flame Ionization Detector (FID). For that purpose the following equipment was used:

HS-autosampler: HS40XI, TurboMatrix 110, Perkin Elmer.
HS-software: HSControl v.2.00, Perkin Elmer.
GC: Autosystem XL, Perkin Elmer.
GC-software: Turbochrom navigator, Perkin Elmer.
Column: HP-FFAP 25 m×0.20 mm×0.33 µm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards. Samples were prepared by adding 200 µl of 4N $H_2SO_4$ to 1 g yoghurt sample and immediately analyzed by HSGC.

Figure 21:
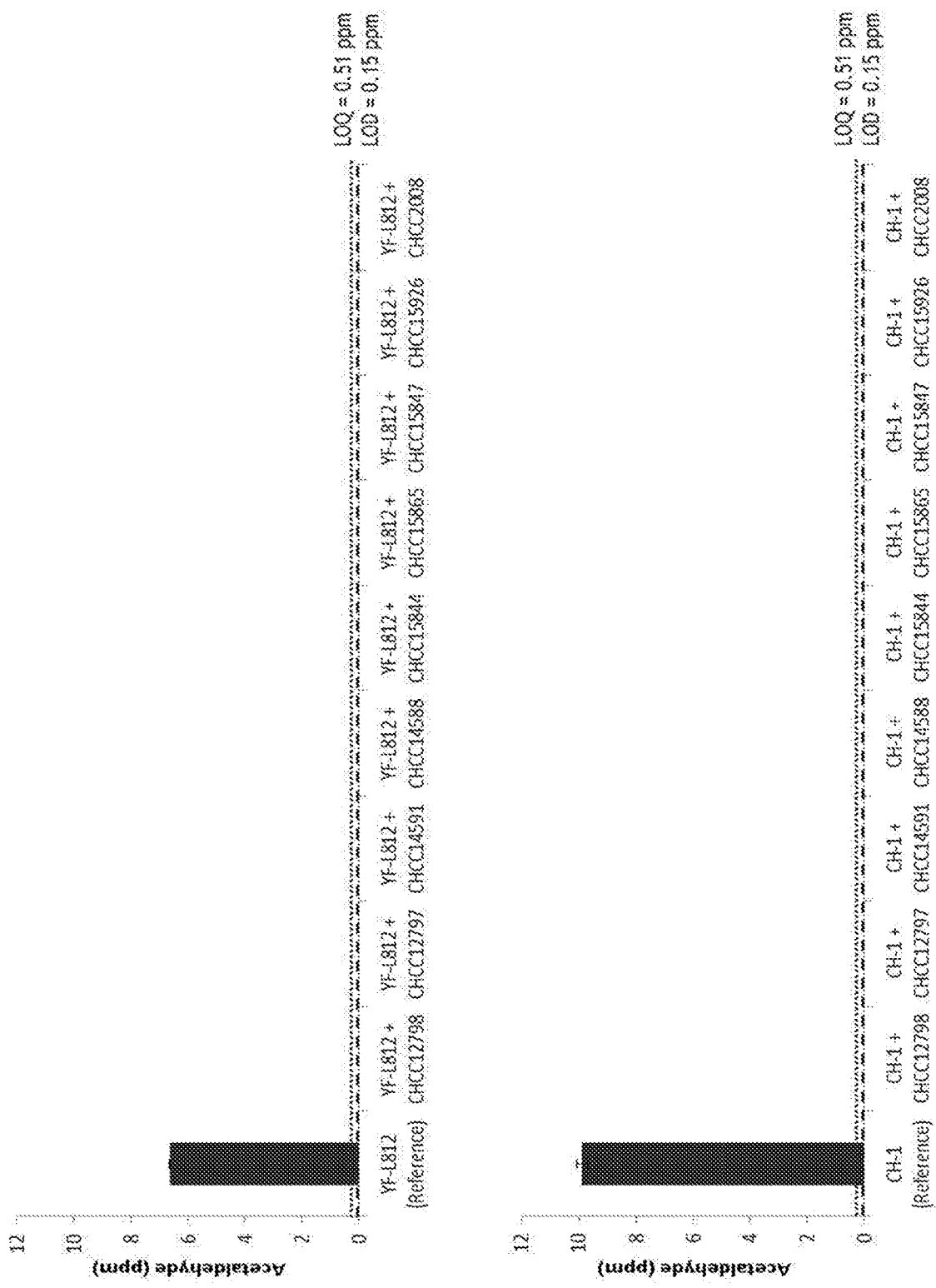
FIG. 21: Acetaldehyde levels after storage at 7±1° C. for 14 days in fermented milk products fermented with starter culture, FD DVS YF-L812 or F-DVS CH-1, alone (Reference), or starter cultures in combination one of the nine Lb. fermentum strains. LOD: Limit of detection. LOQ: Limit of quantification.

The results are illustrated in FIG. 21 and show that each of the strains Lb. fermentum CHCC12798, Lb. fermentum CHCC12797, Lb. fermentum CHCC14591, Lb. fermentum CHCC14588, Lb. fermentum CHCC15844, Lb. fermentum CHCC15865, Lb. fermentum CHCC15847, Lb. fermentum CHCC15926, and Lb. fermentum CHCC2008 has the ability to reduce the concentration of acetaldehyde produced by a starter culture during fermentation in a fermented milk product.

REFERENCES

EP0221499
EP0576780
EP1442113
U.S. Pat. No. 5,378,458
EP2 693 885
EP13717237
EP13714671

Gerez et al., Control of spoilage fungi by lactic acid bacteria, Biological Control, vol. 64 (2013): 231-237

Aunsbjerg et al., Contribution of volatiles to the antifungal effect of *Lactobacillus paracasei* in defined medium and yoghurt, Int J Food Microbiology, vol. 194 (2015): 46-53

Kosikowski, F. V. and Mistry, V. V., "Cheese and Fermented Milk Foods", 1997, 3rd Ed. F. V. Kosikowski, L.L.C. Westport, Conn.

DEPOSITS and EXPERT SOLUTION

The applicant requests that a sample of the deposited micro-organisms stated below may only be made available to an expert, until the date on which the patent is granted.

The *Lactobacillus fermentum* strain CHCC12798 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32084.

The *Lactobacillus fermentum* strain CHCC12797 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32085.

The *Lactobacillus fermentum* strain CHCC14591 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32086.

The *Lactobacillus fermentum* strain CHCC14588 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32087.

The *Lactobacillus fermentum* strain CHCC15844 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No: 32088.

The *Lactobacillus fermentum* strain CHCC15865 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32089.

The *Lactobacillus fermentum* strain CHCC15847 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32090.

The *Lactobacillus fermentum* strain CHCC15848 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32091.

The *Lactobacillus fermentum* strain CHCC15926 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 22 under the accession No.: 32096.

The *Lactobacillus fermentum* strain CHCC2008 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2009 May 19 under the accession No.: 22584.

The *Lactobacillus rhamnosus* strain CHCC15860 was deposited at German Collection of Microorganisms and Cell Cultures (Deutsche Sammlung van Mikroorganismen und Zellkulturen GmbH; DSMZ), Inhoffenstr. 7B, D-38124 Braunschweig deposited on 2015 Jul. 16 under the accession No.: 32092.

The *Penicillium solitum* strain CHCC16948 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32093.

The *Penicillium brevicompactum* strain CHCC16935 was deposited at German Collection of Microorganisms and Cell Cultures (Deutsche Sammlung von Mikroorganismen und Zellkulturen GmbH; DSMZ), Inhoffenstr. 7B, D-38124 Braunschweig deposited on 2015 Jul. 16 under the accession No.: 32094.

The deposits were made according to the Budapest treaty on the international recognition of the deposit of microorganisms for the purposes of patent procedure.

The invention claimed is:

1. A method of producing a fermented milk product, comprising adding Lactobacillus rhamnosus of strain CHCC15860 deposited with the German Collection of Microorganisms and Cell Cultures (DSMZ) under accession number DSM32092 to milk or a milk product to obtain a mixture, and fermenting the mixture at a temperature between about 22° C. and about 43° C. until a pH of less than 4.6 is reached, wherein the *Lactobacillus rhamnosus* of strain CHCC15860 inhibits growth of one or more of the *Penicillium solitum* strain deposited with the DSMZ under accession number DSM32093 and the *Penicillium brevicompactum* strain deposited with the DSMZ under accession number DSM32094.

2. The method of claim 1, wherein the method further comprises producing a food, feed or pharmaceutical product from the fermented milk product.

3. A food, feed or pharmaceutical product obtained by the method of claim 2, wherein the method comprises:
adding the Lactobacillus rhamnosus of strain CHCC15860 to milk or a milk product to obtain a mixture;
fermenting the mixture at a temperature between about 22° C. and about 43° C. until a pH of less than 4.6 is reached to obtain a fermented milk product, and producing a food, feed or pharmaceutical product from the fermented milk product, wherein the *Lactobacillus rhamnosus* of strain CHCC15860 inhibits growth of one or more of the *Penicillium satum* strain deposited with the DSMZ under accession number DSM32093 and the *Penicillium brevicompactum* strain deposited with the DSMZ under accession number DSM32094.

4. A method of producing a fermented milk product, comprising adding a composition comprising *Lactobacillus rhamnosus* of strain CHCC15860 deposited with the German Collection of Microorganisms and Cell Cultures (DSMZ) under accession number DSM32092 to milk or a milk product to obtain a mixture, and fermenting the mixture at a temperature between about 22° C. and about 43° C. until a pH of less than 4.6 is reached, wherein the *Lactobacillus rhamnosus* of strain CHCC15860 inhibits growth of one or more of the *Penicillium solitum* strain deposited with the DSMZ under accession number DSM32093 and the *Penicillium brevicompactum* strain deposited with the DSMZ under accession number DSM32094.

5. The method of claim 4, wherein the method further comprises producing a food, feed or pharmaceutical product from the fermented milk product.

6. A food, feed or pharmaceutical product obtained by the method of claim 5, wherein the method comprises:
adding the composition comprising Lactobacillus rhamnosus of strain CHCC15860 to milk or a milk product to obtain a mixture;
fermenting the mixture at a temperature between about 22° C. and about 43° C. until a pH of less than 4.6 is reached to obtain a fermented milk product, and
producing a food, feed or pharmaceutical product from the fermented milk product, wherein the *Lactobacillus rhamnosus* of strain CHCC15860 inhibits growth of one or more of the *Penicillium sofitum* strain deposited with the DSMZ under accession number DSM32093 and the *Penicillium brevicompactum* strain deposited with the DSMZ under accession number DSM32094.

7. The method of claim 4, wherein the composition further comprises Lactobacillus fermentum of strain CHCC14591 deposited with the DSMZ under accession number DSM32086.

8. The method of claim 4, wherein the composition further comprises a cryoprotective compound.

9. The method of claim 4, wherein the composition is a solid frozen or freeze-dried starter culture comprising lactic acid bacteria in a concentration of at least $10^9$ colony forming units per g (CFU/g) frozen material.

10. The method of claim 4, wherein the composition is a solid frozen or freeze-dried starter culture comprising lactic acid bacteria in a concentration of at least $10^{10}$ CFU/g frozen material.

11. The method of claim 4, wherein the composition is a solid frozen or freeze-dried starter culture comprising lactic acid bacteria in a concentration of at least $10^{11}$ CFU/g frozen material.

12. The method of claim 5, wherein the composition is added in an amount to provide a concentration of the *Lactobacillus rhamnosus* of at least $10^7$ CFU/g.

13. The method of claim 1, further comprising adding *Lactobacillus fermentum* of strain CHCC14591 deposited with the DSMZ under accession number DSM32086 to the milk or milk product.

14. The method of claim 1, wherein the *Lactobacillus rhamnosus* is added at a concentration of at least $10^9$ CFU/g.

* * * * *